(12) United States Patent
Fink et al.

(10) Patent No.: US 7,201,167 B2
(45) Date of Patent: *Apr. 10, 2007

(54) METHOD AND COMPOSITION FOR THE TREATMENT OF LUNG SURFACTANT DEFICIENCY OR DYSFUNCTION

(75) Inventors: James Fink, San Mateo, CA (US); Yehuda Ivri, Newport Beach, CA (US)

(73) Assignee: Aerogen, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/080,279

(22) Filed: Mar. 14, 2005

(65) Prior Publication Data

US 2005/0229926 A1 Oct. 20, 2005

Related U.S. Application Data

(63) Continuation-in-part of application No. 10/957,321, filed on Sep. 30, 2004, which is a continuation-in-part of application No. 10/883,115, filed on Jun. 30, 2004, which is a continuation-in-part of application No. 10/828,765, filed on Apr. 20, 2004.

(51) Int. Cl.
*A61M 15/00* (2006.01)
(52) U.S. Cl. .............................. 128/203.12; 128/204.18
(58) Field of Classification Search ........... 128/200.16, 128/203.12, 204.18, 204.23
See application file for complete search history.

(56) References Cited

U.S. PATENT DOCUMENTS

| 550,315 | A | 11/1895 | Allen |
|---|---|---|---|
| 809,159 | A | 1/1906 | Willis et al. |
| 1,680,616 | A | 8/1928 | Horst |
| 2,022,520 | A | 11/1935 | Philbrick |
| 2,101,304 | A | 12/1937 | Wright |
| 2,158,615 | A | 5/1939 | Wright |
| 2,187,528 | A | 1/1940 | Wing |

(Continued)

FOREIGN PATENT DOCUMENTS

CH 477 885 9/1969

(Continued)

OTHER PUBLICATIONS

Abys, J.A. et al., "Annealing Behavior of Palladium-Nickel Alloy Electrodeposits," Plating and Surface Finishing, Aug. 1996, pp. 1-7.
Allen, T. *Particle Size Measurement*, Third Edition, Chapman and Hall pp. 167-169 (1981).
Ashgriz, N. et al. "Development of a Controlled Spray Generator" Rev. Sci. Instrum., 1987, pp. 1291-1296, vol. 58, No. 7.
Berggren, E. "Pilot Study of Nebulized Surfactant Therapy for Neonatal Respiratory Distress Syndrome", Acta Paediatr 89: 460-464, Taylor & Francis, ISSN 0803-5253, 2000, Sweden.

(Continued)

*Primary Examiner*—Justine Yu
(74) *Attorney, Agent, or Firm*—Townsend and Townsend and Crew LLP

(57) ABSTRACT

A method of treating a disease involving surfactant deficiency or dysfunction in a patient's lungs is disclosed comprising the steps of providing a liquid lung surfactant composition; aerosolizing the lung surfactant composition with a vibrating aperture-type aerosol generator to form a surfactant aerosol; and introducing the surfactant aerosol into the gas flow within a circuit of a pressure-assisted breathing system coupled to the patient's respiratory system, whereby a therapeutically effective amount of said surfactant is delivered to the patient's lungs. Apparatus is also disclosed that increases the efficiency of delivery of aerosolized medicaments such as aerosolized lung surfactant.

12 Claims, 8 Drawing Sheets

U.S. PATENT DOCUMENTS

| | | | |
|---|---|---|---|
| 2,223,541 A | 12/1940 | Baker | |
| 2,266,706 A | 12/1941 | Fox et al. | |
| 2,283,333 A | 5/1942 | Martin | |
| 2,292,381 A | 8/1942 | Klagges | |
| 2,360,297 A | 10/1944 | Wing | |
| 2,375,770 A | 5/1945 | Dahlberg | |
| 2,383,098 A | 8/1945 | Wheaton | |
| 2,404,063 A | 7/1946 | Healy | |
| 2,430,023 A | 11/1947 | Longmaid | |
| 2,474,996 A | 7/1949 | Wallis | |
| 2,512,004 A | 6/1950 | Wing | |
| 2,521,657 A | 9/1950 | Severy | |
| 2,681,041 A | 6/1954 | Zodtner et al. | |
| 2,705,007 A | 3/1955 | Gerber | |
| 2,735,427 A | 2/1956 | Sullivan | |
| 2,764,946 A | 10/1956 | Henderson | |
| 2,764,979 A | 10/1956 | Henderson | |
| 2,779,623 A | 1/1957 | Eisenkraft | |
| 2,935,970 A | 5/1960 | Morse et al. | |
| 3,103,310 A | 9/1963 | Lang | |
| 3,325,031 A | 6/1967 | Singler | |
| 3,411,854 A | 11/1968 | Rosler et al. | |
| 3,515,348 A | 6/1970 | Coffman, Jr. | |
| 3,550,864 A | 12/1970 | East | |
| 3,558,052 A | 1/1971 | Dunn | |
| 3,561,444 A | 2/1971 | Boucher | |
| 3,563,415 A | 2/1971 | Ogle | |
| 3,680,954 A | 8/1972 | Frank | |
| 3,719,328 A | 3/1973 | Hindman | |
| 3,738,574 A | 6/1973 | Guntersdorfer et al. | |
| 3,771,982 A | 11/1973 | Dobo | |
| 3,790,079 A | 2/1974 | Berglund et al. | |
| 3,804,329 A | 4/1974 | Martner | |
| 3,812,854 A * | 5/1974 | Michaels et al. | 128/200.16 |
| 3,838,686 A | 10/1974 | Szekely | |
| 3,842,833 A | 10/1974 | Ogle | |
| 3,865,106 A | 2/1975 | Palush | |
| 3,903,884 A | 9/1975 | Huston et al. | |
| 3,906,950 A | 9/1975 | Cocozza | |
| 3,908,654 A | 9/1975 | Lhoest et al. | |
| 3,950,760 A | 4/1976 | Rauch et al. | |
| 3,951,313 A | 4/1976 | Coniglione | |
| 3,958,249 A | 5/1976 | DeMaine et al. | |
| 3,970,250 A | 7/1976 | Drews | |
| 3,983,740 A | 10/1976 | Danel | |
| 3,993,223 A | 11/1976 | Welker, III et al. | |
| 4,005,435 A | 1/1977 | Lundquist et al. | |
| 4,020,834 A | 5/1977 | Bird | |
| 4,030,492 A | 6/1977 | Simbrumer | |
| 4,052,986 A | 10/1977 | Scaife | |
| 4,059,384 A | 11/1977 | Holland et al. | |
| D246,574 S | 12/1977 | Meierhoefer | |
| 4,076,021 A | 2/1978 | Thompson | |
| 4,083,368 A | 4/1978 | Freezer | |
| 4,094,317 A | 6/1978 | Wasnich | |
| 4,101,041 A | 7/1978 | Mauro, Jr. et al. | |
| 4,106,503 A | 8/1978 | Rsenthal et al. | |
| 4,109,174 A | 8/1978 | Hodgson | |
| 4,113,809 A | 9/1978 | Abair et al. | |
| D249,958 S | 10/1978 | Meierhoefer | |
| 4,119,096 A | 10/1978 | Drews | |
| 4,121,583 A | 10/1978 | Chen | |
| 4,159,803 A | 7/1979 | Cameto et al. | |
| 4,207,990 A | 6/1980 | Weiler et al. | |
| 4,210,155 A | 7/1980 | Grimes | |
| 4,226,236 A | 10/1980 | Genese | |
| 4,240,081 A | 12/1980 | Devitt | |
| 4,240,417 A | 12/1980 | Holever | |
| 4,248,227 A | 2/1981 | Thomas | |
| 4,261,512 A | 4/1981 | Zierenberg | |
| D259,213 S | 5/1981 | Pagels | |
| 4,268,460 A | 5/1981 | Boiarski et al. | |
| 4,294,407 A | 10/1981 | Reichl et al. | |
| 4,298,045 A | 11/1981 | Weiler et al. | |
| 4,299,784 A | 11/1981 | Hense | |
| 4,300,546 A | 11/1981 | Kruber | |
| 4,301,093 A | 11/1981 | Eck | |
| 4,319,155 A | 3/1982 | Makai et al. | |
| 4,334,531 A | 6/1982 | Reichl et al. | |
| 4,336,544 A | 6/1982 | Donald et al. | |
| 4,338,576 A | 7/1982 | Takahashi et al. | |
| 4,340,044 A * | 7/1982 | Levy et al. | 128/204.21 |
| 4,368,476 A | 1/1983 | Uehara et al. | |
| 4,368,850 A | 1/1983 | Szekely | |
| 4,374,707 A | 2/1983 | Pollack | |
| 4,389,071 A | 6/1983 | Johnson, Jr. et al. | |
| 4,408,719 A | 10/1983 | Last | |
| 4,428,802 A | 1/1984 | Kanai et al. | |
| 4,431,136 A | 2/1984 | Janner et al. | |
| 4,454,877 A | 6/1984 | Miller et al. | |
| 4,465,234 A | 8/1984 | Maehara et al. | |
| 4,474,251 A | 10/1984 | Johnson, Jr. | |
| 4,474,326 A | 10/1984 | Takahashi | |
| 4,475,113 A | 10/1984 | Lee et al. | |
| 4,479,609 A | 10/1984 | Maeda et al. | |
| 4,484,577 A * | 11/1984 | Sackner et al. | 128/203.28 |
| 4,502,481 A * | 3/1985 | Christian | 128/205.24 |
| 4,512,341 A | 4/1985 | Lester | |
| 4,530,464 A | 7/1985 | Yamamoto et al. | |
| 4,533,082 A | 8/1985 | Maehara et al. | |
| 4,539,575 A | 9/1985 | Nilsson | |
| 4,544,933 A | 10/1985 | Heinzl | |
| 4,546,361 A | 10/1985 | Brescia et al. | |
| 4,550,325 A | 10/1985 | Viola | |
| 4,566,452 A | 1/1986 | Farr | |
| 4,591,883 A | 5/1986 | Isayama | |
| 4,593,291 A | 6/1986 | Howkins | |
| 4,605,167 A | 8/1986 | Maehara | |
| 4,613,326 A | 9/1986 | Szwarc | |
| 4,620,201 A | 10/1986 | Heinzl et al. | |
| 4,628,890 A | 12/1986 | Freeman | |
| 4,632,311 A | 12/1986 | Nakane et al. | |
| 4,658,269 A | 4/1987 | Rezanka | |
| 4,659,014 A | 4/1987 | Soth et al. | |
| 4,677,975 A | 7/1987 | Edgar et al. | |
| 4,678,680 A | 7/1987 | Abowitz | |
| 4,679,551 A | 7/1987 | Anthony | |
| 4,681,264 A | 7/1987 | Johnson, Jr. | |
| 4,693,853 A | 9/1987 | Falb et al. | |
| 4,702,418 A | 10/1987 | Carter et al. | |
| 4,722,906 A | 2/1988 | Guire | |
| 4,753,579 A | 6/1988 | Murphy | |
| 4,790,479 A | 12/1988 | Matsumoto et al. | |
| 4,793,339 A | 12/1988 | Matsumoto et al. | |
| 4,796,807 A | 1/1989 | Bendig et al. | |
| 4,799,622 A | 1/1989 | Ishikawa et al. | |
| 4,805,609 A | 2/1989 | Roberts et al. | |
| 4,819,629 A | 4/1989 | Jonson | |
| 4,819,834 A | 4/1989 | Thiel | |
| 4,826,080 A | 5/1989 | Ganser | |
| 4,826,759 A | 5/1989 | Guire et al. | |
| 4,828,886 A | 5/1989 | Hieber | |
| 4,843,445 A | 6/1989 | Stemme | |
| 4,849,303 A | 7/1989 | Graham et al. | |
| 4,850,534 A | 7/1989 | Takahashi et al. | |
| 4,852,563 A * | 8/1989 | Gross | 128/202.27 |
| 4,865,006 A | 9/1989 | Nogi et al. | |
| 4,871,489 A | 10/1989 | Ketcham | |
| 4,872,553 A | 10/1989 | Suzuki et al. | |
| 4,877,989 A | 10/1989 | Drews et al. | |
| 4,888,516 A | 12/1989 | Daeges et al. | |
| 4,922,901 A | 5/1990 | Brooks et al. | |
| 4,926,915 A | 5/1990 | Deussen et al. | |
| 4,934,358 A | 6/1990 | Nilsson et al. | |

| | | | | | |
|---|---|---|---|---|---|
| 4,951,661 A * | 8/1990 | Sladek .................. 128/202.27 | 5,355,872 A | 10/1994 | Riggs et al. |
| 4,954,225 A | 9/1990 | Bakewell | 5,357,946 A | 10/1994 | Kee et al. |
| 4,957,239 A | 9/1990 | Tempelman | 5,372,126 A | 12/1994 | Blau |
| 4,964,521 A | 10/1990 | Wieland et al. | 5,383,906 A | 1/1995 | Burchett et al. |
| D312,209 S | 11/1990 | Morrow et al. | 5,388,571 A | 2/1995 | Roberts et al. |
| 4,968,299 A | 11/1990 | Ahlstrand et al. | 5,392,768 A | 2/1995 | Johansson et al. |
| 4,971,665 A | 11/1990 | Sexton | 5,396,883 A | 3/1995 | Knupp et al. |
| 4,973,493 A | 11/1990 | Guire | 5,414,075 A | 5/1995 | Swan et al. |
| 4,976,259 A | 12/1990 | Higson et al. | 5,415,161 A | 5/1995 | Ryder |
| 4,979,959 A | 12/1990 | Guire | 5,419,315 A | 5/1995 | Rubsamen |
| 4,994,043 A | 2/1991 | Ysebaert | 5,426,458 A | 6/1995 | Wenzel et al. |
| 5,002,048 A | 3/1991 | Makiej, Jr. | 5,431,155 A | 7/1995 | Marelli |
| 5,002,582 A | 3/1991 | Guire et al. | 5,435,282 A | 7/1995 | Haber et al. |
| 5,007,419 A | 4/1991 | Weinstein et al. | 5,435,297 A | 7/1995 | Klein |
| 5,016,024 A | 5/1991 | Lam et al. | 5,437,267 A | 8/1995 | Weinstein et al. |
| 5,021,701 A | 6/1991 | Takahashi et al. | 5,445,141 A | 8/1995 | Kee et al. |
| 5,022,587 A | 6/1991 | Hochstein | D362,390 S | 9/1995 | Weiler |
| 5,024,733 A | 6/1991 | Abys et al. | 5,449,502 A | 9/1995 | Igusa et al. |
| 5,046,627 A | 9/1991 | Hansen | 5,452,711 A | 9/1995 | Gault |
| 5,062,419 A | 11/1991 | Rider | 5,458,135 A | 10/1995 | Patton et al. |
| 5,063,396 A | 11/1991 | Shiokawa et al. | 5,458,289 A | 10/1995 | Cater |
| 5,063,922 A * | 11/1991 | Hakkinen .............. 128/200.16 | 5,474,059 A | 12/1995 | Cooper |
| 5,073,484 A | 12/1991 | Swanson et al. | 5,477,992 A | 12/1995 | Jinks et al. |
| 5,076,266 A | 12/1991 | Babaev | 5,479,920 A | 1/1996 | Piper et al. |
| 5,080,093 A | 1/1992 | Raabe et al. | 5,485,850 A | 1/1996 | Dietz |
| 5,080,649 A | 1/1992 | Vetter | 5,487,378 A | 1/1996 | Robertson et al. |
| 5,086,765 A | 2/1992 | Levine | 5,489,266 A | 2/1996 | Grimard |
| 5,086,785 A | 2/1992 | Gentile et al. | 5,497,944 A | 3/1996 | Weston et al. |
| 5,115,803 A | 5/1992 | Sioutas | D369,212 S | 4/1996 | Snell |
| 5,115,971 A | 5/1992 | Greenspan et al. | 5,511,726 A | 4/1996 | Greenspan et al. |
| D327,008 S | 6/1992 | Friedman | 5,512,329 A | 4/1996 | Guire et al. |
| 5,122,116 A | 6/1992 | Kriesel et al. | 5,512,474 A | 4/1996 | Clapper et al. |
| 5,129,579 A | 7/1992 | Conte | 5,515,841 A | 5/1996 | Robertson et al. |
| 5,134,993 A | 8/1992 | Van Der Linden et al. | 5,515,842 A | 5/1996 | Ramseyer et al. |
| 5,139,016 A | 8/1992 | Waser | 5,516,043 A | 5/1996 | Manna et al. |
| 5,140,740 A | 8/1992 | Weigelt | 5,518,179 A | 5/1996 | Humberstone et al. |
| 5,147,073 A | 9/1992 | Cater | 5,529,055 A | 6/1996 | Gueret |
| 5,148,802 A * | 9/1992 | Sanders et al. ........ 128/204.18 | 5,533,497 A | 7/1996 | Ryder |
| 5,152,456 A | 10/1992 | Ross et al. | 5,537,997 A * | 7/1996 | Mechlenburg et al. .. 128/204.23 |
| 5,157,372 A | 10/1992 | Langford | 5,542,410 A | 8/1996 | Goodman et al. |
| 5,164,740 A | 11/1992 | Ivri | 5,549,102 A | 8/1996 | Lintl et al. |
| 5,169,029 A | 12/1992 | Behar et al. | 5,560,837 A | 10/1996 | Trueba |
| 5,170,782 A | 12/1992 | Kocinski | 5,563,056 A | 10/1996 | Swan et al. |
| 5,180,482 A | 1/1993 | Abys et al. | D375,352 S | 11/1996 | Bologna |
| 5,186,164 A | 2/1993 | Raghuprasad | 5,579,757 A | 12/1996 | McMahon et al. |
| 5,186,166 A | 2/1993 | Riggs et al. | 5,582,330 A | 12/1996 | Iba |
| 5,198,157 A | 3/1993 | Bechet | 5,584,285 A * | 12/1996 | Salter et al. ........... 128/200.21 |
| 5,201,322 A | 4/1993 | Henry et al. | 5,586,550 A | 12/1996 | Ivri et al. |
| 5,213,860 A | 5/1993 | Laing | 5,588,166 A | 12/1996 | Burnett |
| 5,217,148 A | 6/1993 | Cater | 5,601,077 A | 2/1997 | Imbert |
| 5,217,492 A | 6/1993 | Guire et al. | 5,609,798 A | 3/1997 | Liu et al. |
| 5,227,168 A | 7/1993 | Chvapil | 5,632,878 A | 5/1997 | Kitano |
| 5,230,496 A | 7/1993 | Shillington et al. | 5,635,096 A | 6/1997 | Singer et al. |
| 5,245,995 A | 9/1993 | Sullivan et al. | 5,637,460 A | 6/1997 | Swan et al. |
| 5,248,087 A | 9/1993 | Dressler | 5,647,349 A | 7/1997 | Ohki et al. |
| 5,258,041 A | 11/1993 | Guire et al. | 5,653,227 A | 8/1997 | Barnes et al. |
| 5,261,601 A | 11/1993 | Ross et al. | 5,654,007 A | 8/1997 | Johnson et al. |
| 5,263,992 A | 11/1993 | Guire | 5,654,162 A | 8/1997 | Guire et al. |
| 5,279,568 A | 1/1994 | Cater | 5,654,460 A | 8/1997 | Rong |
| 5,297,734 A | 3/1994 | Toda | 5,657,926 A | 8/1997 | Toda |
| 5,299,739 A | 4/1994 | Takahashi et al. | 5,660,166 A | 8/1997 | Lloyd |
| 5,303,854 A | 4/1994 | Cater | 5,664,557 A | 9/1997 | Makiej, Jr. |
| 5,309,135 A | 5/1994 | Langford | 5,664,706 A | 9/1997 | Cater |
| 5,312,281 A | 5/1994 | Takahashi et al. | 5,665,068 A | 9/1997 | Takamura |
| 5,313,955 A | 5/1994 | Rodder | 5,666,946 A | 9/1997 | Langenback |
| 5,319,971 A | 6/1994 | Osswald et al. | 5,670,999 A | 9/1997 | Takeuchi et al. |
| 5,320,603 A | 6/1994 | Vetter et al. | 5,685,491 A | 11/1997 | Marks et al. |
| 5,322,057 A | 6/1994 | Raabe et al. | 5,692,644 A | 12/1997 | Gueret |
| 5,342,011 A | 8/1994 | Short | 5,694,923 A * | 12/1997 | Hete et al. ............. 128/204.18 |
| 5,342,504 A | 8/1994 | Hirano et al. | 5,707,818 A | 1/1998 | Chudzik et al. |
| 5,347,998 A | 9/1994 | Hodson et al. | 5,709,202 A | 1/1998 | Lloyd et al. |
| 5,348,189 A | 9/1994 | Cater | 5,714,360 A | 2/1998 | Swan et al. |
| 5,350,116 A | 9/1994 | Cater | 5,714,551 A | 2/1998 | Bezwada et al. |

| | | |
|---|---|---|
| 5,718,222 A | 2/1998 | Lloyd et al. |
| D392,184 S | 3/1998 | Weiler |
| 5,724,957 A | 3/1998 | Rubsamen et al. |
| 5,744,515 A | 4/1998 | Clapper |
| 5,752,502 A | 5/1998 | King |
| 5,755,218 A | 5/1998 | Johansson et al. |
| 5,758,637 A | 6/1998 | Ivri et al. |
| 5,775,506 A | 7/1998 | Grabenkort |
| 5,788,665 A | 8/1998 | Sekins |
| 5,788,819 A | 8/1998 | Onishi et al. |
| 5,790,151 A | 8/1998 | Mills |
| 5,810,004 A | 9/1998 | Ohki et al. |
| 5,819,730 A | 10/1998 | Stone et al. |
| 5,823,179 A | 10/1998 | Grychowski et al. |
| 5,823,428 A | 10/1998 | Humberstone et al. |
| 5,829,723 A | 11/1998 | Brunner et al. |
| 5,836,515 A | 11/1998 | Fonzes |
| 5,839,617 A | 11/1998 | Cater et al. |
| 5,842,468 A | 12/1998 | Denyer et al. |
| 5,862,802 A | 1/1999 | Bird |
| 5,865,171 A | 2/1999 | Cinquin |
| 5,878,900 A | 3/1999 | Hansen |
| 5,893,515 A | 4/1999 | Hahn et al. |
| 5,894,841 A | 4/1999 | Voges |
| 5,897,008 A | 4/1999 | Hansen |
| 5,910,698 A | 6/1999 | Yagi |
| 5,915,377 A | 6/1999 | Coffee |
| 5,918,637 A | 7/1999 | Fleischman |
| 5,925,019 A | 7/1999 | Ljungquist |
| 5,938,117 A | 8/1999 | Ivri |
| 5,950,619 A | 9/1999 | Van Der Linden et al. |
| 5,954,268 A | 9/1999 | Joshi et al. |
| 5,960,792 A | 10/1999 | Lloyd et al. |
| 5,964,417 A | 10/1999 | Amann et al. |
| 5,970,974 A | 10/1999 | Van Der Linden et al. |
| 5,976,344 A | 11/1999 | Abys et al. |
| 5,993,805 A | 11/1999 | Sutton et al. |
| 6,000,396 A | 12/1999 | Melker et al. |
| 6,007,518 A | 12/1999 | Kriesel et al. |
| 6,012,450 A | 1/2000 | Rubsamen |
| 6,014,970 A | 1/2000 | Ivri et al. |
| 6,026,809 A | 2/2000 | Abrams et al. |
| 6,029,666 A | 2/2000 | Aloy et al. |
| 6,032,665 A | 3/2000 | Psaros |
| 6,037,587 A | 3/2000 | Dowell et al. |
| 6,039,696 A | 3/2000 | Bell |
| 6,045,215 A | 4/2000 | Coulman |
| 6,045,874 A | 4/2000 | Himes |
| 6,047,818 A | 4/2000 | Warby et al. |
| 6,055,869 A | 5/2000 | Stemme et al. |
| 6,060,128 A | 5/2000 | Kim et al. |
| 6,062,212 A | 5/2000 | Davison et al. |
| 6,068,148 A | 5/2000 | Weiler |
| 6,085,740 A | 7/2000 | Ivri et al. |
| 6,096,011 A | 8/2000 | Trombley, III et al. |
| 6,105,877 A | 8/2000 | Coffee |
| 6,106,504 A | 8/2000 | Urrutia |
| 6,116,234 A | 9/2000 | Genova et al. |
| 6,123,413 A | 9/2000 | Agarwal et al. |
| 6,139,674 A | 10/2000 | Markham et al. |
| 6,142,146 A | 11/2000 | Abrams et al. |
| 6,145,963 A | 11/2000 | Pidwerbecki et al. |
| 6,146,915 A | 11/2000 | Pidwerbecki et al. |
| 6,152,130 A | 11/2000 | Abrams et al. |
| 6,155,676 A | 12/2000 | Etheridge et al. |
| 6,158,431 A | 12/2000 | Poole |
| 6,161,536 A | 12/2000 | Redmon et al. |
| 6,163,588 A | 12/2000 | Matsumoto et al. |
| 6,182,662 B1 | 2/2001 | McGhee |
| 6,186,141 B1 | 2/2001 | Pike et al. |
| 6,196,218 B1 | 3/2001 | Voges |
| 6,196,219 B1 | 3/2001 | Hess et al. |
| 6,205,999 B1 | 3/2001 | Ivri et al. |
| 6,216,916 B1 | 4/2001 | Maddox et al. |
| 6,223,746 B1 | 5/2001 | Jewett et al. |
| 6,235,177 B1 | 5/2001 | Borland et al. |
| 6,254,219 B1 | 7/2001 | Agarwal et al. |
| 6,269,810 B1 * | 8/2001 | Brooker et al. ........ 128/203.12 |
| 6,270,473 B1 | 8/2001 | Schwebel |
| 6,273,342 B1 | 8/2001 | Terada et al. |
| 6,318,640 B1 | 11/2001 | Coffee |
| 6,328,030 B1 | 12/2001 | Kidwell et al. |
| 6,328,033 B1 | 12/2001 | Avrahami |
| 6,341,732 B1 | 1/2002 | Martin et al. |
| 6,358,058 B1 | 3/2002 | Strupat et al. |
| 6,394,363 B1 | 5/2002 | Arnott et al. |
| 6,402,046 B1 | 6/2002 | Loser |
| 6,405,934 B1 | 6/2002 | Hess et al. |
| 6,427,682 B1 | 8/2002 | Klimowicz et al. |
| 6,443,146 B1 | 9/2002 | Voges |
| 6,443,366 B1 | 9/2002 | Hirota et al. |
| 6,467,476 B1 | 10/2002 | Ivri et al. |
| 6,467,477 B1 * | 10/2002 | Frank et al. ........... 128/203.23 |
| 6,530,370 B1 | 3/2003 | Heinonen |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |
| 6,581,595 B1 | 6/2003 | Murdock et al. |
| 6,615,824 B2 | 9/2003 | Power |
| 6,629,646 B1 | 10/2003 | Ivri |
| 6,640,804 B2 | 11/2003 | Ivri |
| 6,651,650 B1 | 11/2003 | Yamamoto et al. |
| 6,688,304 B2 | 2/2004 | Gonda et al. |
| 6,705,315 B2 | 3/2004 | Sullivan et al. |
| 6,705,316 B2 * | 3/2004 | Blythe et al. .......... 128/204.18 |
| 6,725,858 B2 * | 4/2004 | Loescher ............... 128/200.14 |
| 6,732,944 B2 | 5/2004 | Litherland et al. |
| 6,745,768 B2 | 6/2004 | Colla et al. |
| 6,745,770 B2 | 6/2004 | McAuliffe et al. |
| 6,755,189 B2 | 6/2004 | Ivri et al. |
| 6,769,626 B1 | 8/2004 | Haveri |
| 6,782,886 B2 | 8/2004 | Narayan et al. |
| 6,810,876 B2 | 11/2004 | Berthon-Jones |
| 6,814,071 B2 | 11/2004 | Klimowicz et al. |
| 6,817,361 B2 | 11/2004 | Berthon-Jones et al. |
| 6,840,240 B1 | 1/2005 | Berthon-Jones et al. |
| 6,845,770 B2 | 1/2005 | Klimowicz et al. |
| 6,851,626 B2 | 2/2005 | Patel et al. |
| 6,860,268 B2 * | 3/2005 | Bohn et al. ............ 128/206.21 |
| 6,904,906 B2 * | 6/2005 | Salter et al. ........... 128/200.21 |
| 2001/0013554 A1 | 8/2001 | Borland et al. |
| 2001/0015737 A1 | 8/2001 | Truninger et al. |
| 2002/0011247 A1 | 1/2002 | Ivri et al. |
| 2002/0023650 A1 | 2/2002 | Gunaratnam et al. |
| 2002/0033178 A1 | 3/2002 | Farrell et al. |
| 2002/0036601 A1 | 3/2002 | Puckeridge et al. |
| 2002/0078958 A1 | 6/2002 | Stenzler |
| 2002/0104530 A1 | 8/2002 | Ivri et al. |
| 2002/0121274 A1 | 9/2002 | Borland et al. |
| 2002/0134372 A1 | 9/2002 | Loeffler et al. |
| 2002/0134374 A1 | 9/2002 | Loeffler et al. |
| 2002/0134375 A1 | 9/2002 | Loeffler et al. |
| 2002/0134377 A1 | 9/2002 | Loeffler et al. |
| 2002/0162551 A1 | 11/2002 | Litherland |
| 2002/0195107 A1 | 12/2002 | Smaldone |
| 2003/0140921 A1 | 7/2003 | Smith et al. |
| 2003/0145859 A1 | 8/2003 | Bohn et al. |
| 2003/0150445 A1 | 8/2003 | Power et al. |
| 2003/0150446 A1 | 8/2003 | Patel et al. |
| 2003/0226906 A1 | 12/2003 | Ivri |
| 2004/0000598 A1 | 1/2004 | Ivri |
| 2004/0004133 A1 | 1/2004 | Ivri et al. |
| 2004/0011358 A1 | 1/2004 | Smaldone et al. |

| | | | |
|---|---|---|---|
| 2004/0035413 | A1 | 2/2004 | Smaldone et al. |
| 2004/0035490 | A1 | 2/2004 | Power |
| 2004/0050947 | A1 | 3/2004 | Power et al. |
| 2004/0139963 | A1 | 7/2004 | Ivri et al. |
| 2004/0139968 | A1 | 7/2004 | Loeffler et al. |
| 2004/0188534 | A1 | 9/2004 | Litherland et al. |
| 2004/0194783 | A1 | 10/2004 | McAuliffe et al. |
| 2004/0226561 | A1 | 11/2004 | Colla et al. |
| 2004/0226566 | A1 | 11/2004 | Gunaratnam et al. |
| 2004/0256488 | A1 | 12/2004 | Loeffler et al. |
| 2005/0011514 | A1 | 1/2005 | Power et al. |
| 2005/0039746 | A1 | 2/2005 | Grychowski et al. |
| 2005/0139211 | A1 | 6/2005 | Alston et al. |
| 2005/0150496 | A1 | 7/2005 | Smaldone |
| 2005/0211245 | A1 | 9/2005 | Smaldone et al. |
| 2005/0211253 | A1 | 9/2005 | Smaldone et al. |
| 2005/0220763 | A1 | 10/2005 | Condos et al. |
| 2005/0235987 | A1 | 10/2005 | Smaldone et al. |
| 2005/0284469 | A1 | 12/2005 | Tobia et al. |

FOREIGN PATENT DOCUMENTS

| | | | |
|---|---|---|---|
| CH | 555 681 | | 11/1974 |
| DE | 11 03 522 | | 3/1961 |
| DE | 3513628 | C1 * | 10/1986 |
| EP | 0 049 636 | A1 | 4/1982 |
| EP | 0 103 161 | A2 | 3/1984 |
| EP | 0 134 847 | A1 | 3/1985 |
| EP | 0 178 925 | A2 | 4/1986 |
| EP | 0 387 222 | A1 | 9/1990 |
| EP | 0 432 992 | A1 | 6/1991 |
| EP | 0 476 991 | B1 | 3/1992 |
| EP | 0 480 615 | A1 | 4/1992 |
| EP | 0 510 648 | A2 | 10/1992 |
| EP | 0 516 565 | A1 | 12/1992 |
| EP | 0 542 723 | A2 | 5/1993 |
| EP | 0 933 138 | A2 | 4/1999 |
| EP | 0 923 957 | A1 | 6/1999 |
| EP | 1 142 600 | A1 | 10/2001 |
| GB | 973 458 | | 10/1964 |
| GB | 1 454 597 | | 11/1976 |
| GB | 2 073 616 | A | 10/1981 |
| GB | 2 101 500 | | 1/1983 |
| GB | 2 177 623 | A | 1/1987 |
| GB | 2 240 494 | A | 7/1991 |
| GB | 2 272 389 | A | 5/1994 |
| JP | 57-023852 | | 2/1982 |
| JP | 57-105608 | | 7/1982 |
| JP | 58-061857 | | 4/1983 |
| JP | 58-139757 | | 8/1983 |
| JP | 59-142163 | A | 8/1984 |
| JP | 60-004714 | | 1/1985 |
| JP | 61-008357 | A | 1/1986 |
| JP | 61-215059 | A | 9/1986 |
| JP | 02-135169 | | 5/1990 |
| JP | 02-189161 | | 7/1990 |
| JP | 60-07721 | A | 1/1994 |
| WO | WO 82/03548 | A | 10/1982 |
| WO | WO 92/07600 | A1 | 5/1992 |
| WO | WO 92/11050 | A1 | 9/1992 |
| WO | WO 92/17231 | A1 | 10/1992 |
| WO | WO 93/01404 | A1 | 1/1993 |
| WO | WO 93/10910 | A1 | 6/1993 |
| WO | WO 94/09912 | A1 | 5/1994 |
| WO | WO 96/09229 | | 3/1996 |
| WO | WO 99/17888 | | 4/1999 |
| WO | WO 00/37132 | | 6/2000 |

OTHER PUBLICATIONS

Berglund, R.N., et al. "Generation of Monodisperse Aerosol Standards" Environ. Sci. Technology, Feb. 1973, pp. 147-153, vol. 7, No. 2.

Cipolla, D.C. et al., "Assessment of Aerosol Delivery Systems for Recombinant Human Deoxyribonuclease," S.T.P. Pharma Sciences 4 (1) 50-62, 1994.

Cipolla, D.C. et al., "Characterization of Aerosols of Human Recombinant Deoxyribonuclease I (rhDNase) Generated by Neulizers," Pharmaceutical Research II (4) 491-498, 1994.

Dogan, Aydin PhD, Thesis: "Flexional 'Moonie and Cymbal' Actuators", Penn State University, 1994.

Duarte, Alexander G. et al. "Inhalation Therapy During Mechanical Ventilation" Respiratory Care Clinics of North America, Aerosol Therapy, Jun. 2001, pp. 233-259, vol. 7, No. 2.

Fink, James B. et al. "Aerosol Drug Therapy," Clinical Practice in Respiratory Care; Chapter 12, pp. 308-342; 1999.

Fink, James B. et al. "Aerosol Therapy in Mechanically Ventilated Patients: Recent Advances and New Techniques" Seminars in Respiratory and Critical Care Medicine, 2000, pp. 183-201, vol. 21, No. 3.

Fink, James B. et al. Diagram from and abstract of article entitled "Optimizing efficiency of nebulizers during mechanical ventilation: The effect of placement and type of ventilator circuit" Chest, Oct. 1999, 116:312S.

Gaiser Tool Company catalog, pp. 26, 29-30 (1990).

Gonda, I. "Therapeutic Aerosols", Pharmaceutics, The Science of Dosage Form Design, Editor: M.E. Aulton, 341-358, 1988.

Hancock, B.C. et al., "Molecular Mobility of Amorphous Pharmaceutical Solids Below Their Glass Transition Temperatures," Pharmaceutical Research 12, 799-806 (1995).

Heyder, J. et al., "Deposition of particles in the human respiratory tract in the size range 0.005-15 microns." J Aerosol Sci 17:811-825, 1986.

Hickey, Anthony J. "Pharmaceutical Inhalation Aerosol Technology," Drugs And The Pharmaceutical Science, 1992, pp. 172-173, vol. 54.

Hikayama, H., et al. "Ultrasonic Atomizer with Pump Function" Tech. Rpt. IEICE Japan US88-74:25 (1988).

Jorch, G. Letter to the Editor, "Surfactant Aerosol Treatment of Respiratory Distress Syndrome in Spontaneously Breathing Premature Infants", Pediatric Pulmonology 24: 222-224, 1997, Wiley-Liss.

Maehara, N. et al. "Atomizing rate control of a multi-pinhole-plate ultrasonic atomizer" J. Acoustical Soc. Japan, 1988, pp. 116-121, 44:2.

Maehara, N. et al. "Influence of the vibrating system of a multipinhole-plate ultrasonic nebulizer on its performance" Review of Scientific Instruments, Nov. 1986, p. 2870-2876. vol. 57, No. 1.

Maehara, N. et al. "Influences of liquid's physical properties on the characteristics of a multi-pinhole-plate ultrasonic atomizer" J. Acoustical Soc. Japan 1988, pp. 425-431, 44:6.

Maehara, N. et al. "Optimum Design Procedure for Multi-Pinhole-Plate Ultrasonic Atomizer" Japanese Journal of Applied Physics, 1987, pp. 215-217, vol. 26, Supplement 26-1.

Nogi, T. et al. "Mixture Formation of Fuel Injection System in Gasoline Engine" Nippon Kikai Gakkai Zenkoku Taikai Koenkai Koen Ronbunshu 69:660-662 (1991).

Palla Tech Pd an Pd Alloy Processes—Procedure for the Analysis of Additive IVS in Palla Tech Plating Solutions by HPLC, Technical Bulletin, Electroplating Chemicals & Services, 029-A, Lucent Technologies,, pp. 1-5, 1996.

Siemens, "Servo Ultra Nebulizer 345 Operating Manual," pp. 1-23.

Smaldone, G. C. "Aerosolized Antibiotics: Current and Future", Respiratory Care, 2000, vol. 45, No. 6, pp. 667-675.

Smedsaas-Löfvenbert, A. "Nebulization of Drugs in a Nasal CPAP System", Scandinavian University Press, 1999, Acta Paediatr 88: 89-92, Sweden.

TSI Incorporated product catalog. Vibrating Orifice Aerosol Generator (1989).

Ueha, S., et al. "Mechanism of Ultrasonic Atomization Using a Multi-Pinhole Plate" J. Acoust. Soc. Jpn., 1985, pp. 21-26, (E)6,1.

Wehl, Wolfgang R. "Ink-Jet Printing: The Present State of the Art" for Siemens AG, 1989.

* cited by examiner

METHOD AND COMPOSITION FOR THE TREATMENT OF LUNG SURFACTANT DEFICIENCY OR DYSFUNCTION

CROSS-REFERENCES TO RELATED APPLICATIONS

This application is a continuation-in-part of U.S. application Ser. No. 10/828,765, filed Apr. 20, 2004; U.S. application Ser. No. 10/883,115, filed Jun. 30, 2004; and U.S. application Ser. No. 10/957,321, filed Sep. 9, 2004, the entire contents of which are incorporated by reference herein.

BACKGROUND OF THE INVENTION

This invention relates to methods and compositions for treating diseases that alter the surface active properties of the lung. An important feature in all mammalian lungs is the presence of surface active lining material in the alveoli. These surface active materials are lung surfactants comprised of protein-lipid compositions, e.g. surface active proteins and phospholipids, which are produced naturally in the lungs and are essential to the lungs' ability to absorb oxygen. They facilitate respiration by continually modifying surface tension of the fluid normally present within the air sacs, or alveoli, that line the inside of the lungs. In the absence of sufficient lung surfactant or when lung surfactant functionality is compromised, these air sacs tend to collapse, and, as a result, the lungs do not absorb sufficient oxygen.

Insufficient or dysfunctional surfactant in the lungs results in a variety of respiratory illnesses in both infants and adults. For example, insufficient lung surfactant may manifest itself as respiratory distress syndrome in premature infants ("iRDS"), i.e. those born prior to 32 weeks of gestation, who have not fully developed a sufficient amount of natural lung surfactant. Diseases involving dysfunctional lung surfactant include may adult respiratory disorders such as acute respiratory distress syndrome (ARDS), asthma, pneumonia, acute lung injury (ALI), etc., as well as infant diseases such as meconium aspiration syndrome (MAS), wherein full-term babies have their first bowel movement in the womb and aspirate the meconium into their lungs. In these cases, the amount of lung surfactant may be normal, but surfactant properties have been disrupted by foreign matter, trauma, sepsis and other infection, etc.

Diseases involving surfactant deficiency and dysfunction have historically been treated by the administration of surface active materials to the lungs, sometimes referred to as surfactant (replacement) therapy. For example, surfactant therapy is at present an established part of routine clinical management of newborn infants with iRDS. Usually these surface active materials are naturally-occurring or synthetically engineered lung surfactants, but may also be nonphospholipid substances such as perfluorocarbons. As used herein, the terms "lung surfactant" and "surfactant" contemplate all of these service active materials suitable for use in surfactant therapy. These lung surfactants can be administered in a variety of ways, the simplest being direct instillation of a liquid solution of lung surfactant into the lungs. An initial dose of about 100 mg/kg body weight (BW) is usually needed to compensate for the deficiency of lung surfactant in these babies, and repeated treatment is required in many cases.

An alternative approach is treatment with aerosolized lung surfactant. Aerosol delivery of surfactant to the lungs is usually less efficient than direct instillation, mainly because of large losses of aerosol in the delivery system. In conventional delivery systems, the amount of aerosol reaching the lungs can be further reduced if particle sizes are too large, i.e. >5 μm mass median aerodynamic diameter (MMAD), if aerosol delivery is not coordinated with slow inspiration and breath-hold, or if airways (especially artificial airways) are long and narrow. Estimates of lung delivery of aerosolized surfactants with most conventional delivery systems have been generally less than 1–10% of amount the liquid surfactant placed in the nebulizer.

However, animal work with improved aerosol delivery systems has shown some promise of increased efficiency. The gas exchange and mechanical benefits that have been seen in animal lung models with the aerosol approach were comparable to those seen with the instillation technique, but those benefits were achieved with only a fraction of the conventional 100 mg/kg of body weight (BW) instilled dose (MacIntyre, N. R., "Aerosolized Medications for Altering Lung Surface Active Properties". *Respir Care* 2000;45(3) 676–683). As an example of improved aerosol delivery methods in the prior art, increased deposition of aerosolized surfactant has been achieved in animal models using ultrasonic nebulizers instead of jet nebulizers. Lung surfactant deposition of only 0.15–1.6 mg/kg BW/hour has been reported using jet nebulization, whereas deposition of about 10 mg/kg BW/hour (7–9 mg/kg BW with 50 minute nebulization) has been achieved with ultrasonic nebulization. See, for example, Schermuly R et al; "Ultrasonic Nebulization for Efficient Delivery of Surfactant in a Model of Acute Lung Injury—Impact on Gas Exchange." *Am. J. Respir. Crit. Care Med.;* 1997 156 (2) 445–453.

It has been reported that respiratory support with nasal continuous positive airway pressure ("nCPAP") systems, coupled with early instillation of lung surfactants, may have several advantages in the treatment of neonates with iRDS. This treatment has been found to be effective in decreasing the need for mechanical ventilation, with its accompanying mechanical and infectious risks and pathophysiological effects, but still requires intubation for surfactant treatment. See, for example, "Early Use of Surfactant, NCPAP Improves Outcomes in Infant Respiratory Distress Syndrome"; *Pediatrics* 2004; 11;e560–e563 (as reported online by Medscape Medical News group, Jun. 4, 2004).

Opportunities for aerosol delivery of lung surfactants to infants weighing less that 5 kg. have been limited, largely due to the low minute volumes required and the relatively high flow rates of nebulizers and ventilatory support devices that have been available. It has been demonstrated that pre-term infants, both on and off the ventilator, received less than 1% of the nebulizer dose to their lungs. See "Efficiency of aerosol medication delivery from a metered dose inhaler versus jet nebulizer in infants with bronchopulmonary dysplasia". Pediatr. Pulmonol. 1996 May;21; (5):301–9. There has been little empirical data to suggest that nCPAP would be any more efficient since most animal and in vitro CPAP models have demonstrated less than 3% deposition.

Simultaneous administration of surfactant aerosol therapy (using a jet nebulizer) in conjunction with a CPAP system has been found to be clinically feasible and to result in improved respiratory parameters. See, for example, Jorch G et al; "To the Editor: Surfactant Aerosol Treatment of Respiratory Distress Syndrome in Spontaneously Breathing Premature Infants"; *Pediatric Pulmonology* 24:22–224 (1997); and Smedsaas-Lofvenberg A; "Nebulization of Drugs in a Nasal CPAP System"; *Acta Paediatr* 88: 89–92 (1999). However, the losses of aerosolized lung surfactant and other aerosolized medicaments used in CPAP systems were found to be unacceptably high, mainly because of the continued inefficiency of the delivery system. The authors suggest that as much as 10% of the nebulized surfactant might be expected to enter the pharyngeal tube coupled to the patient's respiratory system, but they did no testing to quantify that delivery estimate. (Jorch G et al, supra).

A number of studies have tried to combine aerosolized surfactant with high-frequency ventilation of the infant with iRDS, and aerosolized surfactants have also been tried in the treatment of airway diseases, e.g. cystic fibrosis and chronic bronchitis, both with mixed success, again because of the inefficiency of the delivery systems used. (McIntyre, supra).

As can be seen by the foregoing discussion, many important respiratory therapies for the treatment of lung surfactant deficiency or dysfunction have not been cost-effective or practical to pursue due to the inefficiencies of existing aerosol delivery technology. The present invention is directed to a method of treating these diseases through improved aerosol generation and delivery.

BRIEF SUMMARY OF THE INVENTION

The present invention provides an improved method of treating a disease involving surfactant deficiency or dysfunction in a patient's lungs. In one embodiment, the method of the present invention comprises the steps of providing a liquid lung surfactant composition; aerosolizing the lung surfactant composition with a vibrating aperture-type aerosol generator to form a lung surfactant aerosol; and introducing the lung surfactant aerosol into the gas flow within a circuit of a pressure-assisted breathing system, preferably a CPAP system, coupled to the patient's respiratory system, whereby a therapeutically effective amount of the lung surfactant is delivered to the patient's lungs. Preferred lung surfactants comprise natural surfactants derived from the lavage of animal lungs and synthetically engineered lung surfactants.

In one embodiment, the vibrating aperture-type aerosol generator of the present invention allows the use of a liquid surfactant composition, e.g. a lung surfactant composition having a concentration from 20 mg/ml to 120 mg/ml. The diluent may be any pharmaceutically acceptable diluent, e.g. water or a saline solution.

In another embodiment, 10–90%, preferably greater than 30%, of the active lung surfactant provided to the aerosol generator is delivered to the patient's airway and is inhaled by the patient. Preferably, 5–50% of the active lung surfactant is actually deposited in the patient's lungs. In the practice of the present invention, a therapeutically effective amount of lung surfactant delivered to the patient's lungs (a "unit dose") may be in the range of 2–400 mg. Flow rates of vibrating aperture-type aerosol generators of the present invention may be in the range of 0.1–0.5 ml/min, which is considerably higher than the flow rate of comparable aerosol generators. Preferred delivery rates of active surfactant to the patient's airway are in the range of 2–800 mg/hr. Preferably, the aerosol generator may be adjusted to produce a surfactant particle size of less than 5 μm MMAD, most preferably 1–3 μm MMAD.

The pressure-assisted breathing system utilized in the present invention, preferably a CPAP system, may be designed to further improve the efficiency of the delivery of aerosolized medicaments, including aerosolized surfactants. In one embodiment, the aerosol generator may be positioned so as to introduce aerosolized lung surfactant into the relatively low-volume flow in the respiratory circuit between the main flow of a CPAP system and the patient airway, thereby eliminating the dilution effect that can occur when the aerosol is introduced into the relatively high-volume flow in the pressure-generating circuit.

In another embodiment, the aerosol generator may be positioned so as to introduce surfactant aerosol into a plenum chamber located outside the direct breathing circuit of the CPAP system, thereby collecting a concentration of surfactant aerosol higher than generated by the aerosol generator alone, prior to discharging the surfactant aerosol into the respiratory circuit.

In another embodiment, the circuit of the pressure-assisted breathing system into which the aerosolized lung surfactant is introduced may be provided with a gently angled, preferably straight, path for the flow of aerosol particles from the point at which the aerosol generator introduces the aerosolized lung surfactant into the gas flow to the point at which the aerosolized lung surfactant enters the patient's respiratory system. This design minimizes the amount of aerosol particles that may be trapped at corners in the inner walls of the tubes, deposited at irregular surfaces and obstructions in the tubes or other elements of the circuit, or diverted by sharply angled conduits in the circuit, e.g. those present in conventional "Y", "T" or "V"-shaped junction devices used for connecting the various circuits.

In yet another embodiment, the aerosol generator may be coupled with means for discontinuing the introduction of aerosolized surfactant into the circuit to reduce the amount of aerosolized surfactant lost to the atmosphere during the expiration phase of the respiration cycle.

DETAILED DESCRIPTION OF THE INVENTION

Figure 1:
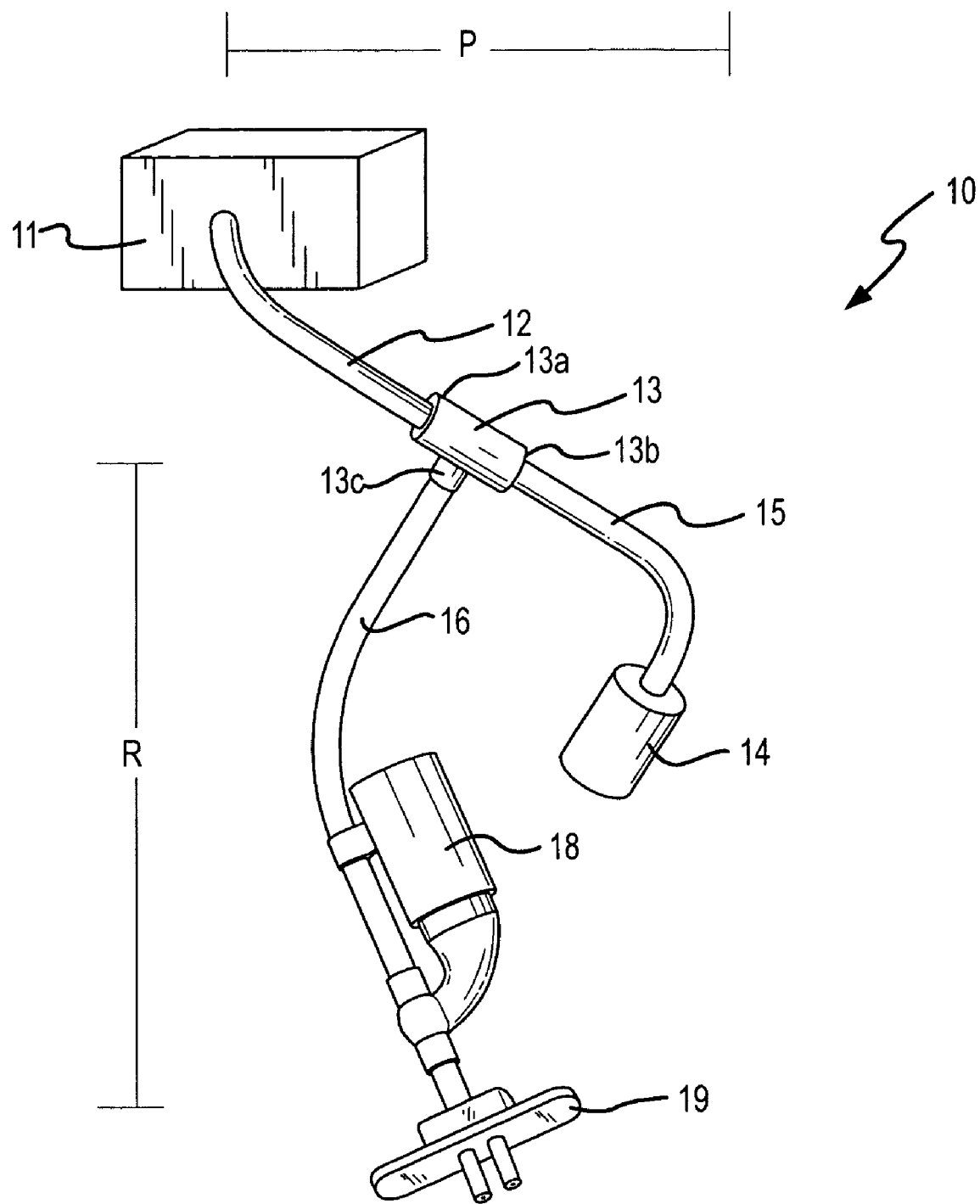
FIG. 1 is a schematic illustration of one embodiment of a CPAP system with a nebulizer containing a vibrating aperture-type aerosol generator.

In one embodiment, the present invention is directed to a method of treating diseases involving surfactant deficiency (also known as "surfactant depletion syndromes") or diseases involving surfactant dysfunction (also known as "surfactant dysfunction syndromes"). Such diseases include, but are not limited to, infant respiratory distress syndrome (iRDS), acute respiratory distress syndrome (ADRS), meconium aspiration syndrome (MAS), asthma, pneumonia (all kinds, including ventilator associated pneumonia), persistent pulmonary hypertension of the newborn (PPHN), congenital diaphragmatic hernia (CDH), sepsis, acute lung injury (ALI), bronchiolitis, COPD-chronic bronchitis, cystic fibrosis, lung transplantation diseases and respiratory syncitial virus (RSV). Since methods for treating such diseases generally involve the administration to the patient's lung of a naturally-occurring (animal-derived) or synthetic (engineered) lung surfactant, the subject methods are sometimes referred to in the art as "surfactant (replacement) therapies".

Generally, the method of the present invention comprises the steps of providing a liquid lung surfactant composition; aerosolizing the lung surfactant composition with an aerosol generator, preferably a vibrating aperture-type aerosol generator, to form an aerosolized lung surfactant (also referred to herein as "surfactant aerosol"); and introducing the surfactant aerosol into the gas flow within a circuit of a pressure-assisted breathing system, preferably a CPAP system, coupled to the patient's respiratory system, whereby a therapeutically effective amount of surfactant is delivered to the patient's lungs.

Lung surfactants are complex and highly surface-active materials, generally composed of lipids and/or proteins. Their principal property is to reduce the surface tension in the lungs and protect the lungs from injuries and infections caused by inhaled particles and microorganisms. The composition of naturally-occurring lung surfactant may vary with various factors such as species, age, and general health of the subject. Therefore, the definition of what a natural lung surfactant is or what should be included in a synthetic lung surfactant composition is dependent on the situation. Surfactant isolated from lung lavage of healthy mammals contain about 10% protein and 90% lipids, of which about 80% are phospholipids and about 20% are neutral lipids, including about 10% unesterified cholesterol.

Lung surfactants are typically high in viscosity and difficult to administer. The lung surfactant may be admixed with a pharmaceutically acceptable diluent, e.g. water or a saline solution, to provide a liquid surfactant composition. In the practice of the present invention, liquid lung surfactant compositions are preferred, for example, liquid surfactant compositions having a concentration of from 20–120 mg/ml, preferably 20–80 mg/ml. Commercially available lung surfactants may already be presented as ready-mixed liquids, and are contemplated as also being useful in the present invention. Examples of commercially available lung surfactant compositions are natural surfactant compositions marketed under the trademarks CUROSURF (Chiesi Pharmaceuticals), ALVEOFACT (Boehringer Ingelheim) and SURVANTA (Abbott Laboratories); and synthetic surfactant compositions marketed under the trademarks EXOSURF (Glaxo Wellcome) and SURFAXIN (Discovery Laboratories).

Aerosol generators permit aerosol formation in a wide variety of ways, e.g. single-substance jet, atomization by centrifugal force, condensation, vaporization, dispersion, ultrasound, jet nebulization, etc. Vibrating aperture-type aerosol generators are preferred in the practice of the present invention. Vibrating aperture-type aerosol generators comprise a unique dome-shaped aperture plate containing over 1000 precision-formed tapered holes, surrounded by a vibrational element. When energy is applied, the aperture plate vibrates over 100,000 times per second. This rapid vibration causes each aperture to act as a micropump, drawing liquid in contact with the plate through the holes to form consistently sized droplets. The result is a low-velocity liquid aerosol optimized for maximum lung deposition. Preferred vibrating aperture-type aerosol generators aerosolize liquids very efficiently, leaving virtually no residual liquid, and operate without using propellants or generating heat, thereby preserving a surfactant's molecular integrity. Representative vibrating aperture-type aerosol generators are described in detail in U.S. Pat. Nos. 5,164,740; 5,586,550; 5,758,637; and 6,085,740, the entire disclosures of which are incorporated herein by reference. Apertures in the aperture plate may be shaped to enhance the rate of droplet production while maintaining droplets within a specified size range, e.g. as described in co-pending U.S. patent application Ser. No. 09/822,573, filed Mar. 30, 2001, incorporated by reference herein. Such apertures may be particularly useful for aerosolizing viscous surfactant compositions in accordance with the present invention. Preferred vibrating aperture-type aerosol generators are commercially available from Aerogen, Inc., Mountain View, Calif.

In general, a nebulizer containing the aerosol generator is positioned so as to introduce the surfactant aerosol produced by the aerosol generator directly into the gas flow within a circuit of a pressure-assisted breathing system coupled to the subject patient's respiratory system. As used herein, the term "pressure-assisted breathing system" means any artificial ventilation system that applies continuous or intermittent pressure, usually positive (i.e. above a certain baseline such as atmospheric pressure), to gas(es) in or about a patient's airway as a means of augmenting movement of gases into the lungs. Any pressure-assisted breathing system is contemplated as being useful in the present invention, e.g. standard CPAP, nCPAP and Bi-level CPAP systems as well as mechanical ventilators that perform the breathing function for the patient and/or provide CPAP to assist in spontaneous breathing by the patient.

CPAP systems support spontaneous breathing by the patient and typically comprise a pressure-generating circuit for maintaining a positive pressure within the system, a patient interface device coupled to a patient's respiratory system and a respiratory circuit for providing gas communication between the pressure-generating circuit and the patient interface device. CPAP systems utilize a constant positive pressure during inhalation to increase and maintain lung volumes and to decrease the work by a patient during spontaneous breathing. The positive pressure effectively dilates the airway and prevents its collapse. The delivery of positive airway pressure is accomplished through the use of a positive air flow source ("flow generator") that provides oxygen or a gas containing oxygen through a flexible tube connected to a patient interface device such as nasal prongs (cannula), nasopharyngeal tubes or prongs, an endotracheal tube, mask, etc. CPAP systems typically maintain and control continuous positive airway pressure by using a restrictive air outlet device, e.g. a fixed orifice or threshold resistor, or a pressure valve, which modulates the amount of gas leaving the circuit to which the patient interface device is attached. This pressure regulating device may be placed at, before or beyond the patient interface device and defines a primary pressure-generating circuit. Reference is made to the aforementioned co-pending U.S. application Ser. No. 10/828,765, filed Apr. 20, 2004; U.S. application Ser. No. 10/883,115, filed Jun. 30, 2004; and U.S. application Ser. No. 10/957,321, filed Sep. 9, 2004 for a more detailed description of CPAP systems suited for use with aerosolized medicaments generally, and particularly suited for the practice of the present invention. Use of such CPAP systems in combination with a vibrating aperture-type aerosol generator considerably enhances the efficiency of delivery of the surfactant aerosol to the patient's lungs.

FIG. 1 illustrates CPAP system 10, which is particularly suited for use with neonates and infants. The primary pressure-generating circuit P may comprise a gas conduit, e.g. flexible tube (inspiratory limb) 12, that receives the high-volume flow of gas generated by flow generator 11. Flexible tube 12 conducts the flow of gas through junction unit 13 to flexible tube (expiratory limb) 15, which continues to transport the flow of gas to pressure-regulating device 14. Pressure-regulating device 14 may be connected to a controller (not shown) that regulates the pressure in the system to the desired CPAP. Respiratory circuit R may comprise a gas conduit, e.g. flexible tube 16, that connects with nebulizer 18, which is connected to patient interface device 19, either directly (as shown) or through a short section of flexible tube 16. As previously described, nebulizer 18 containing a vibrating aperture-type aerosol generator is preferably placed in close proximity to patient interface device 19. Flexible tube 16 is preferably relatively thin, smaller in diameter and more flexible than flexible tubes 12 and 15. For example, flexible tube 16 may be commercially available silicone tubing having an outside diameter of about 5 mm. The increased flexibility of flexible tube 16 allows the patient's head to more freely move about without disconnecting the patient interface device 19 from the patient.

Flow generator 11 may conveniently comprise any of the known sources of pressurized gas suitable for use with pressure-assisted breathing systems. Typically, the flow generator is capable of supplying a flow of high-volume gas, which includes at least some portion of oxygen, at slightly greater than atmospheric pressure. For example, the source of pressurized gas may be an air blower or a ventilator, or the pressurized gas may originate from a wall supply of air and/or oxygen, such as that found within hospitals and medical facilities, or may originate from a pressurized cylinder or cylinders. The pressurized gas may comprise various known mixtures of oxygen with air, nitrogen, or other gases and may be provided in a single stream or flow to circuit P.

Pressure-regulating device 14 may comprise any of the known devices for controlling and maintaining air pressure within a CPAP system at the desired level. Typically, pressure-regulating device 14 may comprise a restrictive air outlet device such as a pressure valve or threshold resistor that modulates the flow of gas leaving the pressure-regulating circuit P. This resistance to air flow may be varied so that the continuous positive airway pressure conducted by respiratory circuit R to patient interface device 19 will suit the needs of the particular patient using the apparatus. Although pressure-regulating device 14 is typically placed downstream of junction unit 13, it may also be placed at or upstream to junction 13.

Junction unit 13 is the point at which respiratory circuit R is in gas communication with primary pressure-generating circuit P. In the CPAP system shown in FIG. 1, junction unit 13 comprises a "T" or "Y"-shaped hollow unit (sometimes referred to as the "WYE") to which flexible tubes 12, 15 and 16 are coupled. As shown in FIG. 1, junction unit 13 may comprise an inlet arm 13a and an outlet arm 13b, which together define a primary gas conduit through the body of junction unit 13. Respiratory arm 13c defines a branch gas conduit that depends from and is in gas communication with the primary gas conduit. Inspiratory limb 12 from flow generator 11 is coupled to the upstream opening in inlet arm 13a and expiratory limb 15 leading to pressure-regulating device 14 is coupled to the downstream opening in outlet arm 13b to form pressure-generating circuit P. Flexible tube 16 is coupled to the downstream opening of respiratory arm 13c and, together with patient interface device 19, forms respiratory circuit R.

Patient interface device 19 is coupled to nebulizer 18, either directly or through a short section of flexible tube of the same size and material as tubing 16. Patient interface device may include any of the known devices for providing gas communication between the CPAP device and the patient's respiratory system. By way of example, the patient interface device may include nasal prongs (as shown), an oral/nasal mask, a nasal mask, nasopharyngeal prongs, an endotracheal tube, a tracheotomy tube, a nasopharyngeal tube, and the like.

Figure 2:
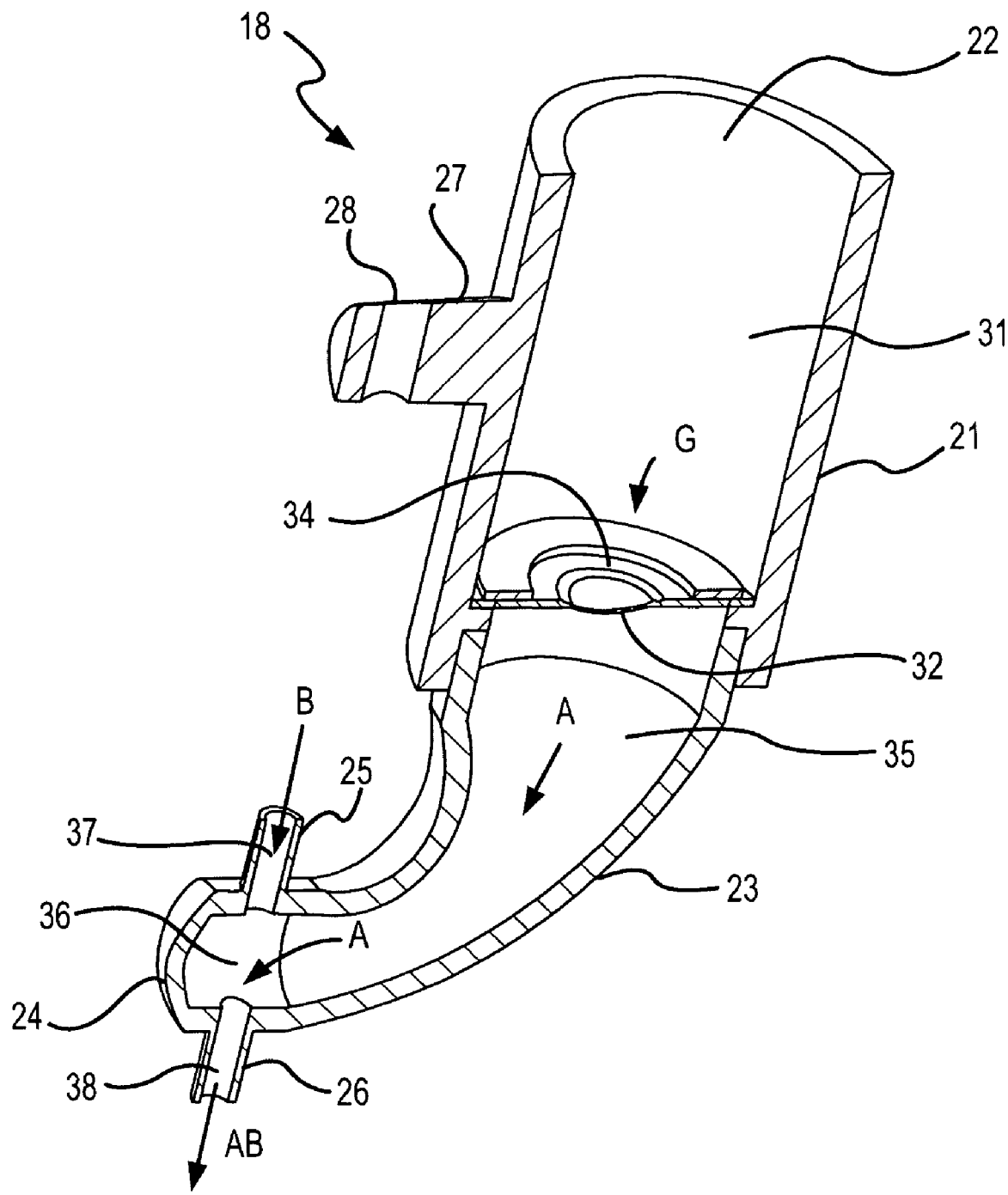
FIG. 2 is a side, cross-sectional view of the nebulizer of FIG. 1.

Nebulizer apparatus 18 is disposed in respiratory circuit R between primary pressure-generating circuit P and patient interface device 19 so as to emit an aerosolized surfactant into the flow of gas in respiratory circuit R that is inhaled by the patient. Vibrating aperture-type nebulizer apparatus are preferred for the practice of this invention. In one embodiment of the present invention, the nebulizer comprises a "miniature" nebulizer 18 such as illustrated in FIG. 2, or as embodied in the latest version of the Pulmonary Drug Delivery System (PDDS) nebulizer marketed by Aerogen, Inc. Nebulizer 18 may comprise a body 21 having relatively small dimensions, e.g. about 15 mm in outside diameter and about 20 mm in length. Body 21 may have an upper medicament port 22 at one end and may be coupled to arm 23 at the other end. At its distal end, arm 23 includes connector unit 24 having an inlet nipple 25 and outlet nipple 26. Connector 24 may be used to connect nebulizer 18 to respiratory circuit R (see FIG. 1) by slipping the downstream end of tube 16 over inlet nipple 25 and attaching the patient interface device 19 directly to outlet nipple 26 or through a short section of tube 16. Body 21 may also include a clip holder 27 including notched channel 28, which is adapted to clip over flexible tube 16 to further secure and support nebulizer 18 on tube 16. Nebulizer 18 is preferably lightweight, for example, having a net weight (without contained liquid) of 5 gms or less, most preferably 3 gms or less. Particularly preferred nebulizers of the present invention may have a net weight of 1–2 gms.

Nebulizer 18 may comprise a reservoir 31 within body 21 for holding a liquid surfactant composition to be delivered to patient's respiratory system and a vibrating aperture-type aerosol generator 32 for aerosolizing the liquid surfactant. Upper medicament port 22 may be provided for delivering the liquid surfactant into reservoir 31 and a removable plug (not shown) may be provided to seal medicament port 22. Reservoir 31 may be sized to accommodate a small volume of surfactant composition, e.g. a volume of 4 ml or less, and preferably a volume of 1–3 ml. Aerosol generator 32 may be positioned at lower medicament outlet 34 of reservoir 31 so that the liquid surfactant composition flows by gravitational action from the reservoir 31 to aerosol generator 32 (Flow G).

Aerosol generator 32 may comprise a piezoelectric element and a vibratable member having a plurality of tapered apertures extending between a first surface and a second surface thereof. Representative vibratable aperture-type aerosol generators are described in detail in U.S. Pat. Nos. 5,164,740; 5,586,550; 5,758,637; and 6,085,740, the entire disclosures of which are incorporated herein by reference. In general, the first surface of the vibratable member, which faces upwardly, receives the liquid medicament from reservoir 31, and the aerosolized medicament is generated at the second surface of the vibratable member when droplets of medicament are ejected from the apertures upon vibration of the vibratable member. Aerosol generators of the present invention are preferably small and light-weight, for example, about 1 gm.

Aerosol generator 32 is positioned so as to facilitate flow of liquid surfactant composition from the reservoir 31 to the aerosol generator 32 and to facilitate passage of the aerosolized surfactant from the aerosol generator 32 into arm 23. Arm 23 may comprise a supply conduit 35 in fluid communication with aerosol generator 32 at one end and connector unit 24 at the other end so as to conduct a flow of aerosolized surfactant (Flow A) toward connector 24. Connector 24 may comprise a gas conduit 36, which is defined on one end by inlet conduit 37 in inlet nipple 25 and at the other end by outlet conduit 38 in outlet nipple 26. The gas conduit 36 of connector 24 may be quite small, e.g. less than 10 cc in volume for infant applications, thereby decreasing dead space in the respiratory circuit. The placement of aerosol generator 32 between reservoir 31 and the respiratory circuit allows reservoir 31 to be opened at medicament port 22 to add liquid surfactant composition without interrupting the pressure of gas flow B in flexible tubing 16. Other nebulizer designs may create a major leak in the pressure circuit when the reservoir is open to the atmosphere.

The downstream end of flexible tubing 16 (see FIG. 1) may be coupled to inlet nipple 25 of connector 24 to conduct gas flow B in the respiratory circuit into inlet conduit 37 to gas conduit 36 of connector 24. Flow A of aerosolized surfactant in supply conduit 35 passes into gas conduit 36 of connector 24 and the aerosolized surfactant is entrained in gas conduit 36 with Flow B. The entrained mixture of aerosolized surfactant and gas (Flow AB) then passes out of the gas conduit 36 through outlet conduit 38 in outlet nipple 26 and to the respiratory system of the patient.

Nebulizer apparatus 18 may be connected to a controller (not shown) for controlling operation of and to supply power to the aerosol generator. Preferably, the controller and other electronic components are connected with wires, cables and connectors that are small and flexible. Examples of other components that may also be associated with nebulizer apparatus 18 are a timer, status indication means, liquid medicament supply nebule or syringe, etc., all as known by those skilled in the art and described in detail in the aforementioned patent and patent applications.

Vibrating aperture-type aerosol generators have several aerosol delivery characteristics that make them uniquely suited for aerosolized medicaments in general, and in particular, for surfactant replacement therapy in accordance with the present invention. Vibrating aperture-type aerosol generators are extremely efficient at producing aerosol particles, aerosolizing nearly 100% of the liquid surfactant that comes into direct contact with the aperture plate. This characteristic virtually eliminates one source of surfactant loss in the system.

In addition, vibrating aperture-type aerosol generators deliver a low-velocity aerosol of precisely defined average particle size. Aerosol particle size distribution and drug output can be modified by changing aperture size in the vibrating plate to meet the needs of a particular patient or situation. Preferably, aerosol particle size is adjusted to less than 5 μm mass median aerodynamic diameter (WAD), and most preferably 1–3 μm MMAD, so as to maintain optimum efficiency. These smaller aerosol particles contribute to enhanced delivery and peripheral pulmonary deposition of the surfactant aerosol, thereby reducing aerosol loss in the system. Vibrating aperture-type aerosol generators also do not create significant heat or shear that can change the characteristics and properties of the surfactant composition.

Aerosol output (flow rate) for vibrating aperture-type aerosol generators of the present invention is considerably higher than other types of nebulizers, and as a result, treatment times for the method of the present invention are considerably shorter than conventional surfactant therapies. For example, a therapeutic amount ("unit dose") of aerosolized surfactant deposited in a patient's lung may be in the range of 2–400 mg. In the practice of the invention, liquid surfactant composition may comprise a solution having a concentration of 20–120 mg/ml. Flow rates for vibrating aperture-type aerosol generators of the present invention are in the range of 0.1–0.5 ml/min, which is considerably higher than the flow rate of comparable aerosol generators, e.g. jet nebulizers typically have a flow rate of less than 0.2 ml/min. If a unit dose of aerosolized surfactant for treatment of surfactant deficiency in a 1 kg neonate is 40 mg (e.g. 1.0 ml of a 40 mg/ml liquid surfactant composition), the method of the present invention using a vibrating aperture-type aerosol generator with a flow rate of 0.4 ml/min will generate 90% of the unit dose in less than 3 minutes, whereas a comparable jet nebulizer would require a fill volume of 3 ml and may deliver the same unit dose in more than 6 minutes. The lower dose requirement and shorter treatment times achieved by the method of the present invention considerably improves the likelihood that the patient will receive benefit prior to direct instillation, or require a treatment protocol with a much lower amount of liquid surfactant placed in the nebulizer. In preferred embodiments, the delivery rate of active surfactant delivered to the lungs of the patient is preferably in the range of 2–800 mg/hr.

In preferred embodiments, the small diameter and size of the reservoir holding the liquid surfactant composition in the nebulizer having a vibrating aperture-type aerosol generator allows the nebulizer to be placed directly into the respiratory circuit without adding a large "rebreathed volume". For example, preferred vibrating aperture-type aerosol generators of the present invention may not add more than about 5 ml of rebreathed volume. As used herein, "rebreathed volume" is the volume of gas required in the system to produce the desired amount of aerosolized surfactant in a confined space. Pneumatic and jet nebulizers typically have reservoir volumes of 6–20 ml, so that placement of one of these nebulizers in the respiratory circuit of a CPAP system between the main flow and the patient's airway adds an undesirable increase in rebreathed volume in the circuit. This increase in rebreathed volume has a dilutive effect on the aerosolized surfactant and reduces the efficiency of the delivery system.

In addition to the previously discussed improved aerosol output and efficiency contributed by the vibrating aperture-type aerosol generator of the invention, the efficiency of the present invention may further be improved by designing the pressure-assisted breathing system in ways that substantially reduce the amount of any aerosolized medicament lost in the system. As one example, the aerosol generator may be positioned so as to introduce the surfactant aerosol into the respiratory circuit of the CPAP system (as shown in FIG. 1), thereby eliminating the dilution effect caused by introducing the surfactant aerosol into the relatively high-volume flow of the pressure-generating circuit, as described in detail in this application's parent, U.S. Ser. No. 10/828,765, filed Apr. 20, 2004, and incorporated by reference herein.

In one preferred embodiment that may be used for any aerosolized medicament, and is particularly useful in surfactant therapy, surfactant aerosol from a vibrating aperture-type aerosol generator may be generated into a plenum chamber of 5–400 ml internal volume located outside the direct breathing circuit (e.g. respiratory circuit R in FIG. 1). The plenum chamber allows a concentration of surfactant aerosol to be collected that is higher than the concentration that is generated by the aerosol generator alone, prior to being discharged into the respiratory circuit. It has been found that the use of the plenum chamber provides an inhaled mass of aerosol surfactant that is comparable to a breath actuated nebulizer, e.g. an inhaled mass of 80% of the surfactant provided to the nebulizer, in less than 25% of the time required for the breath actuated nebulizer to deliver the same inhaled mass.

Figure 3:
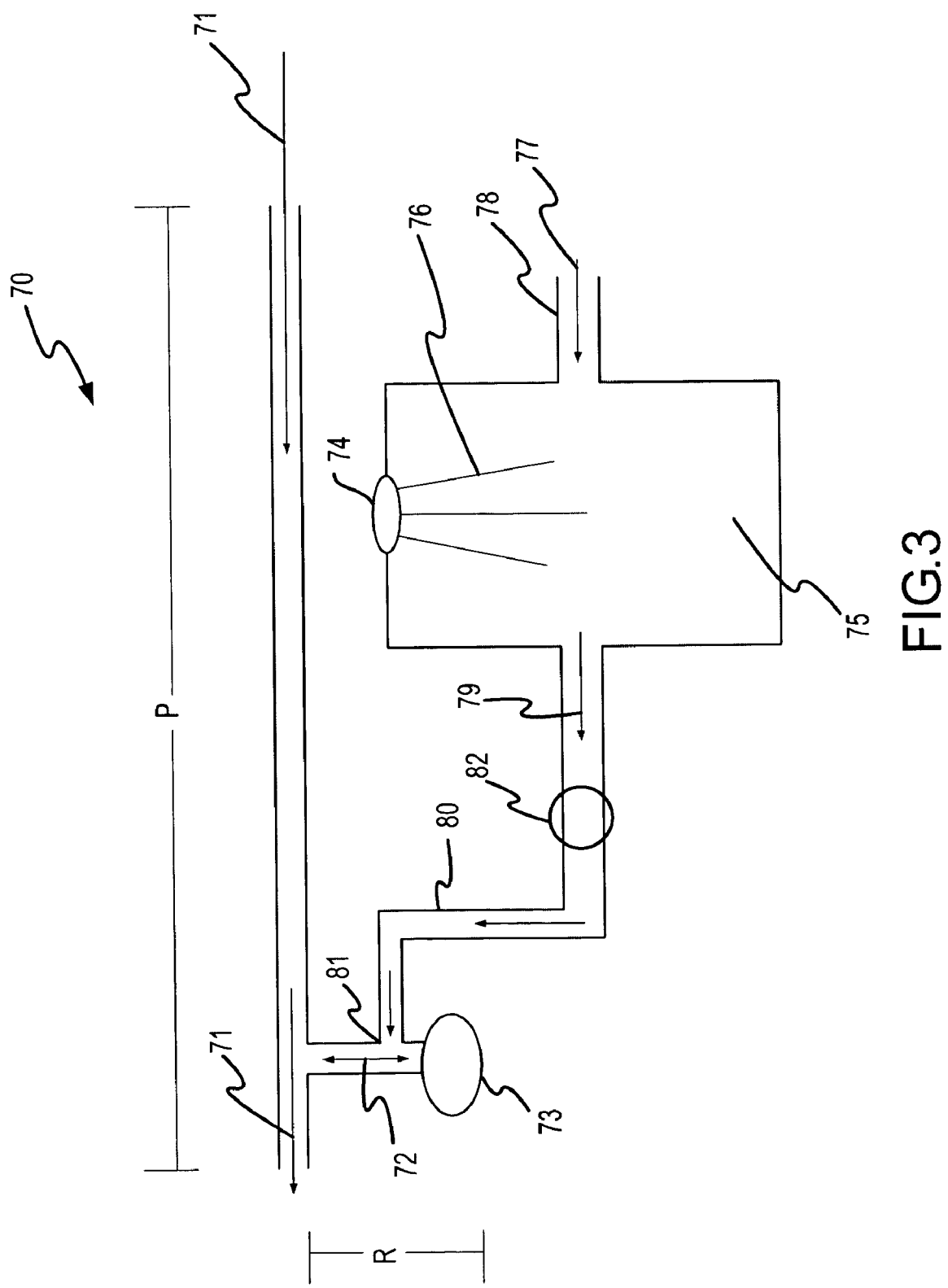
FIG. 3 is a diagrammatic representation of an embodiment of the present invention employing a plenum chamber.

As one example of apparatus using a plenum chamber according to the present invention, FIG. 3 illustrates a CPAP system 70, such as described above in connection with FIG. 1, wherein a main gas flow 71 is carried in pressure-generating circuit P and respiratory flow 72 is carried in respiratory circuit R from circuit P to patient 73. A vibrating aperture-type aerosol generator 74 is located above plenum chamber 75 so as to collect surfactant aerosol 76 generated by aerosol generator 74 in plenum chamber 75. Plenum chamber 75 is sized so that the plume of surfactant aerosol 76 does not impact the wall or bottom of plenum chamber 75, thereby reducing any resulting impactive losses of surfactant aerosol. A controlled secondary gas flow 77 may be introduced into plenum chamber 75 through inlet 78 to drive a flow 79 of concentrated surfactant aerosol from plenum chamber 75 into respiratory flow 72 through conduit 80, which intersects respiratory circuit R at a point 81 proximal to the airway of patient 73. Conduit 80 may have a one-way valve or solenoid 82 that controls flow 79 to respiratory circuit R so as to isolate the volume of gas in plenum chamber 75 from being rebreathed volume; i.e. so that gas flow 79 from plenum chamber 75 is a small percentage of respiratory flow 72. Flow 79 may be continuous or intermittent, with surfactant aerosol being introduced into respiratory circuit R during a discrete part of the respiratory cycle.

In another embodiment, the efficiency of delivery of aerosolized surfactant according to the present invention may be significantly increased in certain pressure-assisted breathing systems by eliminating the sharp angles or corners encountered by the flow of aerosol particles in the circuits of the pressure-assisted breathing system, described in detail in co-pending application U.S. Ser. No. 10/883,115, filed Jun. 30, 2004, and incorporated herein by reference. The efficiency of the delivery of aerosolized surfactant to the patient's lungs may be enhanced by providing a straight or gently angled path for the flow of surfactant aerosol particles from the point at which the aerosol generator introduces the surfactant aerosol particles into the gas flow to the point at which the surfactant aerosol particles enter the patient's respiratory system. This design minimizes the amount of surfactant aerosol particles that may be trapped at corners in the inner walls of the tubes, deposited at irregular surfaces and obstructions in the tubes or other elements of the circuit, or be diverted by sharply angled paths in the circuit.

Figure 4:
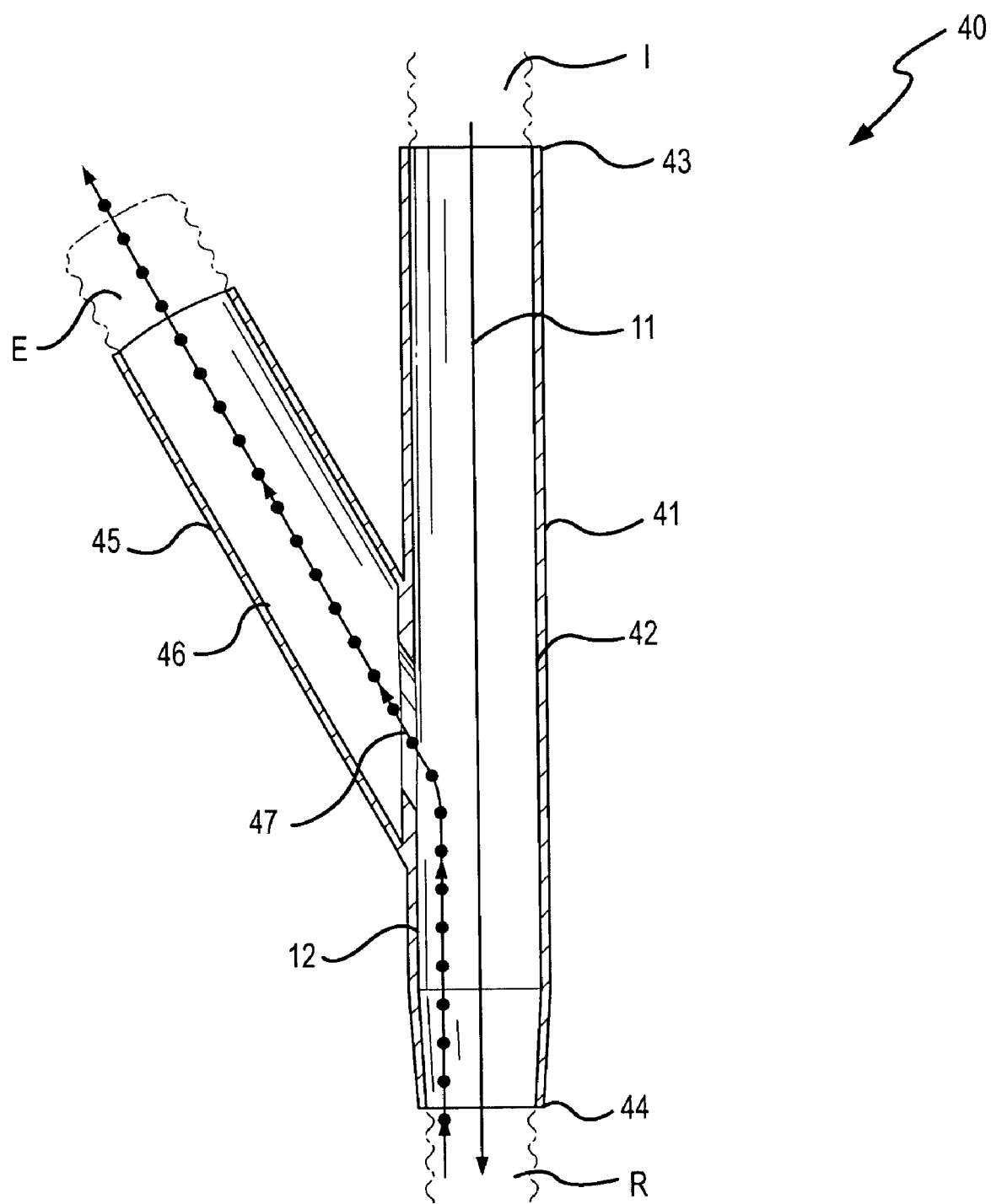
FIG. 4 is a cross-sectional view of a junction device that may be used in the practice of the present invention.

As one example of the aforementioned design, FIG. 4 illustrates a junction device 40 for connecting the various flexible tubes comprising the circuits of a pressure-assisted breathing system that may replace conventional "Y", "T" or "V-shaped junction devices (e.g. element 13 in FIG. 1). Junction device 40 may comprise a tubular main body member 41 having a straight longitudinal lumen 42 connecting an opening in a first end 43 attachable to the inspiratory tube of a inspiratory circuit I and an opening in a second end 44 attachable to the respiratory circuit R. Junction device 40 may further comprise a tubular branch member 45 having a lumen 46 that communicates at one end with lumen 42 at intermediate opening 47, and with expiratory circuit E. Gas flow 11, which contains particles of surfactant aerosol emitted by an aerosol generator into the inspiratory tube I, passes from inspiratory tube I into lumen 42 through the opening in first end 43. It can be seen that junction device 40 provides for gas flow 11 (containing aerosolized surfactant) to follow a straight unobstructed path to respiratory circuit R without any portion being diverted into branch member 45. In other words, there is virtually no change in the angle of the path of gas flow 11. As a result, the full amount of aerosol particles of surfactant contained in gas flow 11 is efficiently delivered through respiratory circuit R to the patient. Upon expiratory effort by the patient, expiratory gas flow 12 follows a path from respiratory circuit R through lumen 42 to lumen 46 of branch member 45 and through expiratory tube E back to the ventilator (not shown).

Figure 5:
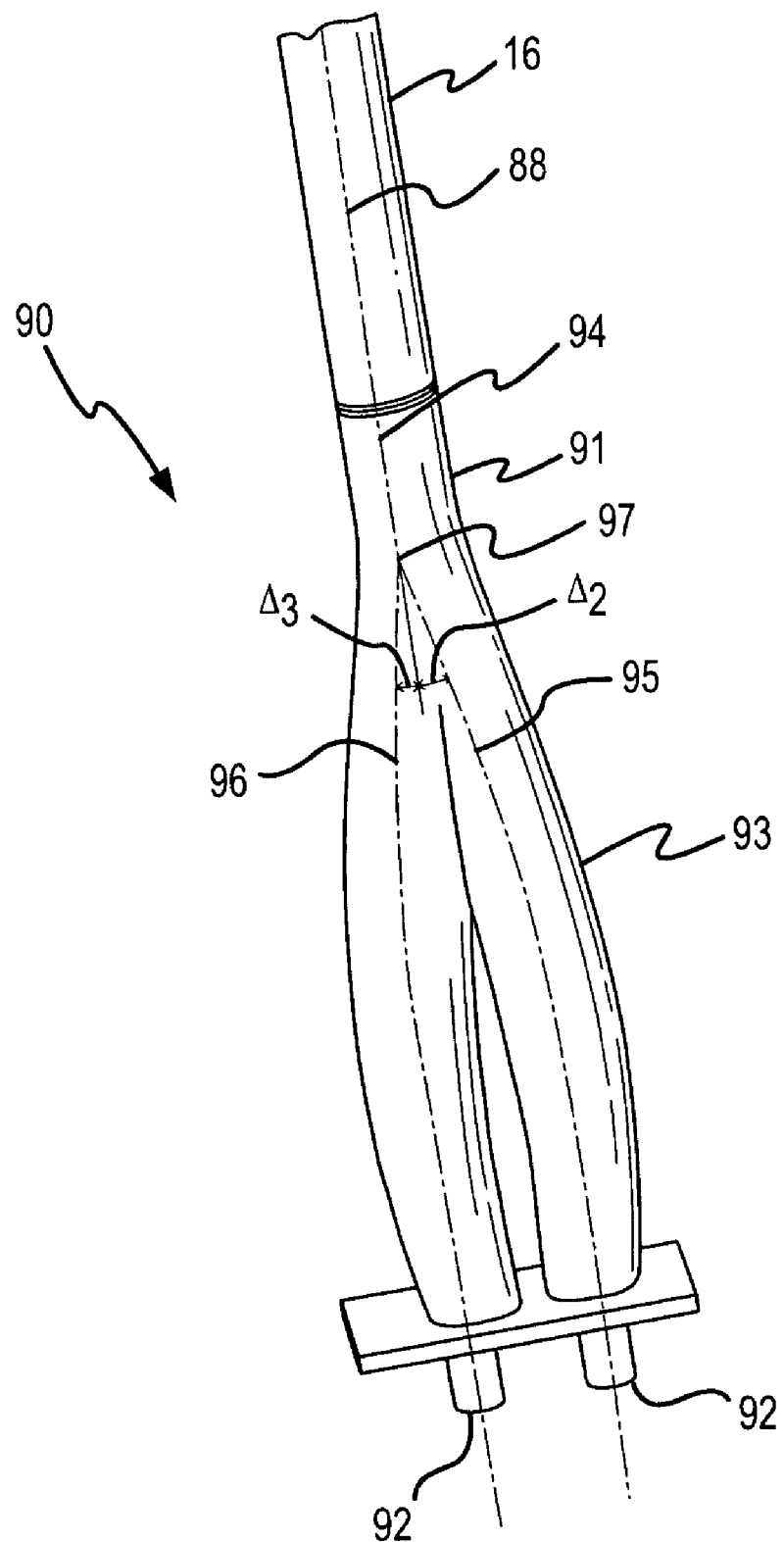
FIG. 5 is a cross-sectional view of an improved nasal cannula that may be used in the practice of the present invention.

In another embodiment, nasal cannula 19 of FIG. 1 may be replaced with nasal cannula 90, illustrated in FIG. 5. Nasal cannula 90 comprises a tubular inlet section 91 connected to a pair of nasal cannula 92 by a tubular forked section 93. Lumen 94 in inlet section 91 is in fluid communication with substantially parallel lumens 95 and 96 in each prong of forked section 93 to provide a gently forked conduit extending from inlet section 91 to nasal cannula 92. Air flow 88 containing surfactant aerosol particles emitted by nebulizer 18 (see FIG. 1) is conducted by respiratory tube 16 (FIG. 1) through lumen 94 in inlet section 91 to intersection 97, where the path of aerosol particles is split so as to follow lumens 95 and 96 to cannula 92. The change in angle between the path for aerosol particles defined by lumen 94 and each of the lumens 95 and 96 at intersection 97 is relatively small; i.e. angles $\Delta_2$ and $\Delta_3$ are no greater than about 15°. As a result, substantially all of the surfactant aerosol particles contained in gas flow 88 reach the nasal cannula 92 and ultimately the patient's nostrils. Because there is minimal loss of aerosol particles in the nasal cannula of the present invention, the efficiency of delivery of the aerosolized surfactant is significantly enhanced.

As still another example of how the efficiency of delivery of aerosolized surfactant according to the present invention may be increased, the aerosol generator (e.g. contained within nebulizer 18 of FIG. 1) may be coupled with means for discontinuing the introduction of aerosolized surfactant into the CPAP circuit, e.g. a flow sensor may be positioned in an auxiliary circuit, to reduce the amount of aerosolized surfactant lost to the atmosphere during the expiration phase of the respiratory cycle, as set forth generally for all aerosolized medicaments in co-pending U.S. application Ser. No. 10/957,321, filed Sep. 9, 2004, and incorporated by reference herein. Preferred flow sensors are adapted to detect small changes is the volumetric flow rate of gas in the auxiliary circuit and send a corresponding electronic signal to the aerosol generator to stop the production of aerosol when the patient exhales.

Figure 6:
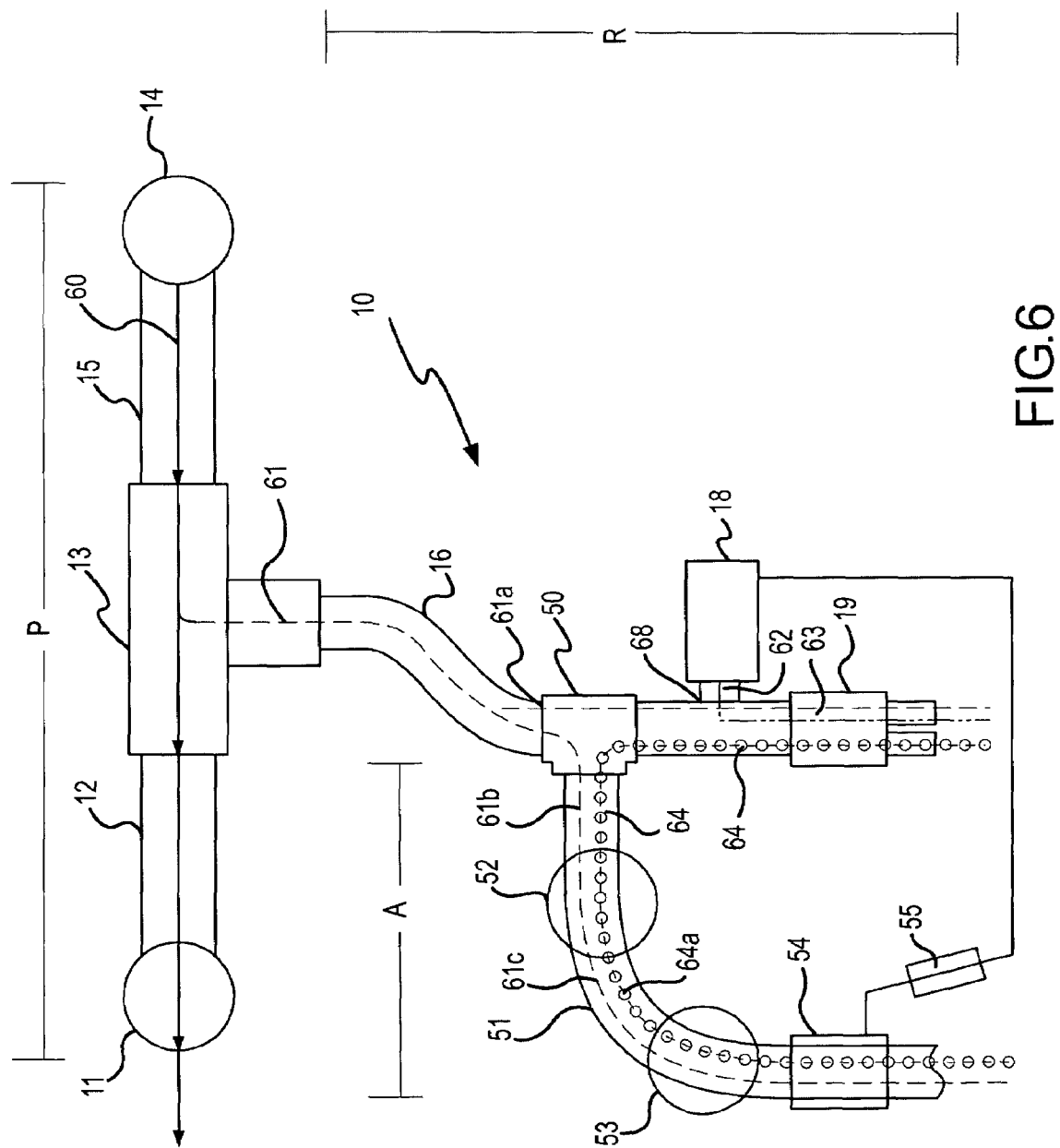
FIG. 6 is a cross-sectional view of a CPAP system with auxiliary flow sensor circuit that may be used in the practice of the present invention.

FIG. 6 represents auxiliary circuit A coupled with the CPAP system 10 illustrated in FIG. 1. Reference numbers in FIGS. 1 and 5 are the same for the same elements in CPAP system 10. Auxiliary circuit A includes flexible tube 51, preferably having the same outside diameter as respiratory tube 16, which connects flow sensor 54 with tube 16 at "T"-shaped junction unit 50. Junction unit 50 is preferably positioned close to nasal cannula 19, but upstream to nebulizer 18 so that surfactant aerosol particles emitted by nebulizer 18 are not diverted into tube 51. Adjustable orifice valve 52 may be positioned in tube 51 between junction 50 and flow sensor 54 to adjust the flow rate of gas passing through flow sensor 54, preferably to the middle of the optimal flow range for sensor 54. Disposable filter 53 may be positioned in tube 51 between junction 50 and flow sensor 54 to remove any bacterial, viral and/or other contaminants from the patient's diseased respiratory system that may be carried by the exhaled air passing through flow sensor 54.

During the operation of CPAP system 10, a high volume flow of gas 60 is introduced into circuit P from flow generator 14 and passes through conduit 15 to pressure-regulating device 11 which maintains a continuous positive pressure throughout the system. Inspiratory flow 61, which may typically be about 10% of flow 60, flows from conduit 15 of pressure-generating circuit P into tube 16 of respiratory circuit R to provide a relatively constant inspiratory flow rate of air to the patient's respiratory system, thereby assisting in the patient's inspiratory efforts in accordance with conventional CPAP system principles. At junction 50, a portion 61a of inspiratory flow 61 proceeds through tube 16 to nasal cannula 19, and a portion 61b of inspiratory flow 61 is diverted through tube 51 to flow sensor 54.

Flow 61a passes through junction 68, at which point aerosolized surfactant particles 62 produced by the aerosol generator of nebulizer 18 are introduced into flow 61a. Resulting flow 63 containing entrained surfactant aerosol particles 62 ultimately passes into the patient's respiratory system through nasal cannula 19, thereby delivering the aerosolized surfactant to the patient's respiratory system. Flow 61b passes through tube 51 and adjustable orifice valve 52, which may be adjusted to reduce the rate of flow 61b to a reduced flow 61c, e.g. a flow rate that may be about 20% of the flow rate of flow 61b. Reduced flow 61c then proceeds through disposable filter 53 to flow sensor 54, and is ultimately released to the atmosphere. As flow 61c passes through flow sensor 54, flow sensor 54 measures the volumetric flow rate of flow 61c and generates a first electronic signal, e.g. a certain output voltage, in electronic circuitry 55 of CPAP system 10 that is characteristic of flow 61c. Since flow 21c is directly proportional to inspiratory flow 21, the first electronic signal caused by flow 61c may be used by the system to identify when the patient is inhaling and continue the delivery of aerosolized surfactant.

When the patient exhales, expiratory flow 64 passes through nasal cannula 19 to tube 16 and is diverted through tube 51 at junction unit 50. Expiratory flow 64 is combined with inspiratory flow 61b in tube 51 to produce a flow rate equal to the sum of the flow rates of flow 64 and 61b. The combination of flow 64 and flow 61b passes through adjustable orifice valve 52 and the total flow rate is reduced in the same manner as previously described for flow 61b alone (identified in FIG. 5 as a combination of flow 61c and 64a). Disposable filter 53 removes any bacterial, viral or other contaminants that may have been present in the combined air flow as a result of flow 64a and the combined air flow then passes through flow sensor 54. When the combination of flow 61c and 64a passes through flow sensor 54, the change (increase) in flow rate over that of flow 61c alone is detected by flow sensor 54. As a result, flow sensor 54 generates a second electronic signal in electronic circuitry 55 that is different than the first electronic signal produced by flow 61c alone. The second electronic signal is transmitted by electronic circuitry 55 to nebulizer 18 and causes it to turn off its aerosol generator. This inactivation of the aerosol generator stops the introduction of aerosol particles 62 into flow 61a. Since the second electronic signal is generated by the volumetric flow rate of the combination of flow 61c and 64a, it indicates the presence of expiratory flow 64. Therefore, the second electronic signal may be used by the system to identify when the patient is exhaling and stop the introduction of aerosolized surfactant. In this way, no aerosol is introduced into tube 16 when the patient exhales, and therefore, no aerosolized surfactant is entrained in expiratory flow 64, which is ultimately released to the atmosphere and lost.

When expiratory effort by the patient stops and inhalation commences again, expiratory flow 64 discontinues and only inspiratory flow 61 is present in the system. As a result, only flow 61c passes through tube 51. Flow sensor 54 detects this change (decrease) in flow rate and generates the first electronic signal, which is transmitted to nebulizer 18. The first electronic signal causes nebulizer 18 to turn on the aerosol generator and resume the introduction of surfactant aerosol particles 62 into flow 61a. The turning on and off of the aerosol generator of nebulizer 18 in concert with the patient's respiratory cycle allows aerosolized surfactant to be introduced into the CPAP system of the present invention only when the patient is inhaling. This results in a dramatic increase in the efficiency of delivery of the surfactant and a corresponding reduction in losses of surfactant to the atmosphere.

As the result of the unique combination of an aerosol generator, preferably a vibrating aperture-type aerosol generator, with a pressure-assisted breathing system, preferably a CPAP system having one or more or the efficiency-improving features set forth above and in the aforementioned co-pending patent applications, from 10–80% of the lung surfactant may be inhaled by the patient in the method of the present invention. In particularly preferred embodiments, greater than 30% of the lung surfactant may be delivered to the patient's lungs.

The following example will illustrate the increase in efficiency resulting from the practice of the present invention, but the present invention is not limited to the details set forth therein. For example, the following example is not limited to the delivery of any particular aerosolized medicament.

Figure 7A:
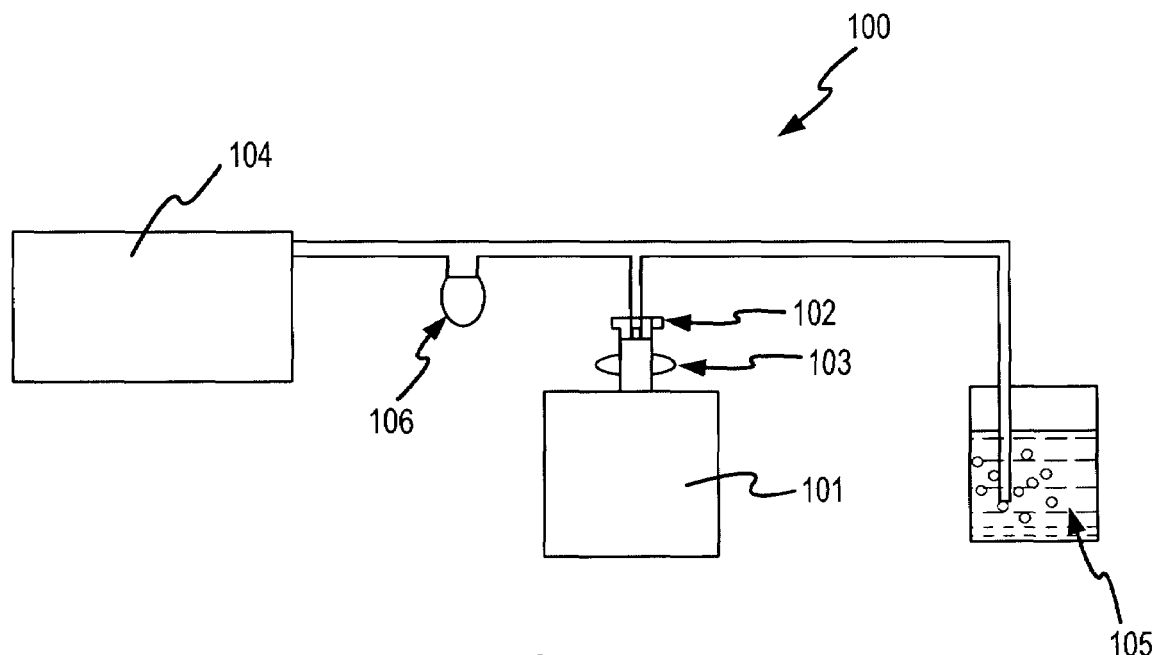
FIGS. 7a and 7b are diagrammatic representations of models used for measuring aerosol delivery with simulated infant breathing pattern during nCPAP.
Figure 7B:
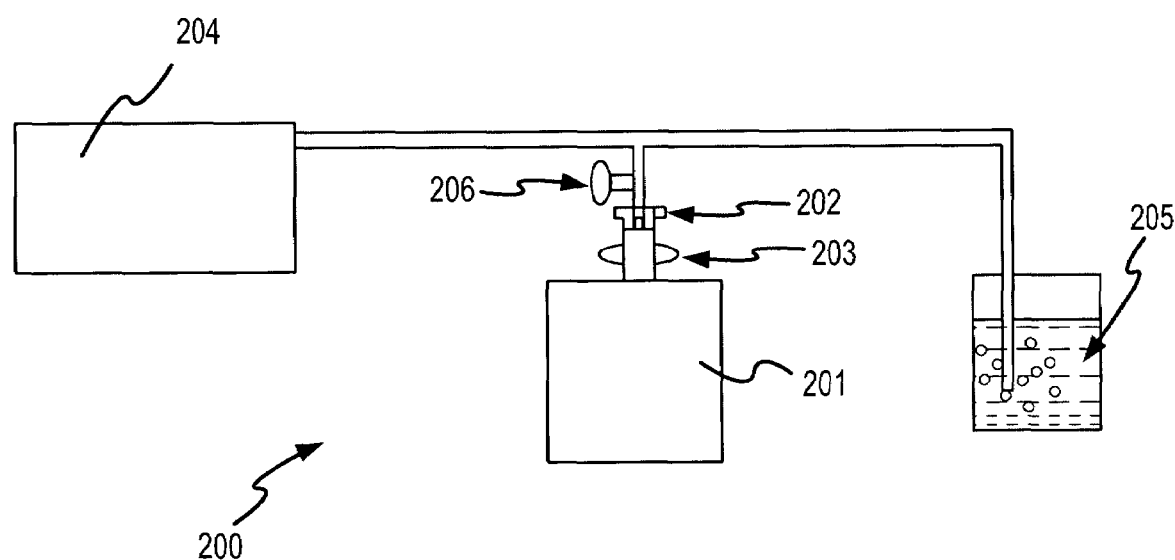

FIGS. 7a and 7b are diagrams of nCPAP systems 100 and 200 that may be used for measuring aerosol delivery with a simulated infant breathing pattern during nasal continuous positive airway pressure (nCPAP). nCPAP systems 100 and 200 comprise breath simulators 101 and 201, consisting of adapters with orifices representing infant size nasal prongs 102 and 202 (Argyle; n=3) connected to absolute filters 103 and 203, attached to reciprocating pump animal ventilators 104 and 204 (Harvard Apparatus) to form a nCPAP system. Lung simulators 100 and 200 may be set to infant ventilatory parameters (VT 10 ml, respiratory rate 40 breaths per minute). A constant oxygen flow of 10 L/min from ventilators 104 and 204 may be used to generate a CPAP of 5 cm $H_2O$ regulated by threshold resistors 105 and 205.

In both systems, a liquid medicament (0.5 mL of 0.5% albuterol sulfate) may be aerosolized with a nebulizer 106 and 206 placed in a circuit of the nCPAP system. Drug may be collected on filters 103 and 104 placed distal to the nasal prongs 102 and 202, and the collected drug may be assayed using High Pressure Liquid Chromatography (HPLC). Care should be taken to assure that only aerosol reaches the filters, and that condensate remains in the breathing circuit, nebulizer or adapter. This may be accomplished by tilting the system so that nebulizers 106 and 206 are lower than respective filter elements 103 and 203. The efficiency of the nCPAP system may then be measured by expressing the amount of drug collected on the filter as a percentage of the drug dose placed in the nebulizer.

In Example 1, nebulizer 106 may comprise a standard jet nebulizer placed so as to discharge aerosolized medicament into the main air flow in the pressure-generating circuit of nCPAP system 100, as shown in FIG. 7a. In Example 2, nebulizer 106 may comprise a nebulizer having a vibrating aperture-type aerosol generator (Aeroneb® Pro from Aerogen, Inc.), also placed so as to discharge aerosolized medicament into the main air flow in the pressure-generating circuit of NCPAP system 100. In Example 3, nebulizer 206 may comprise a small, lightweight nebulizer designed to be suitable for placement proximal to an infant's airway and employing a vibrating aperture-type aerosol generator (Pulmonary Drug Deliver System (PDDS) nebulizer from Aerogen, Inc.), in accordance with one embodiment of the present invention. As shown in FIG. 7b (and in FIG. 1), nebulizer 206 may be placed so as to continuously discharge aerosolized medicament into the lower air flow in the respiratory circuit of nCPAP system 200 between the main air flow and the simulated patient airway, in accordance with another embodiment of the present invention. In Example 4, aerosolized medicament may be generated intermittently from PDDS nebulizer 206 with aerosol generation interrupted during exhalation, in accordance with another embodiment of the present invention.

Figure 8:
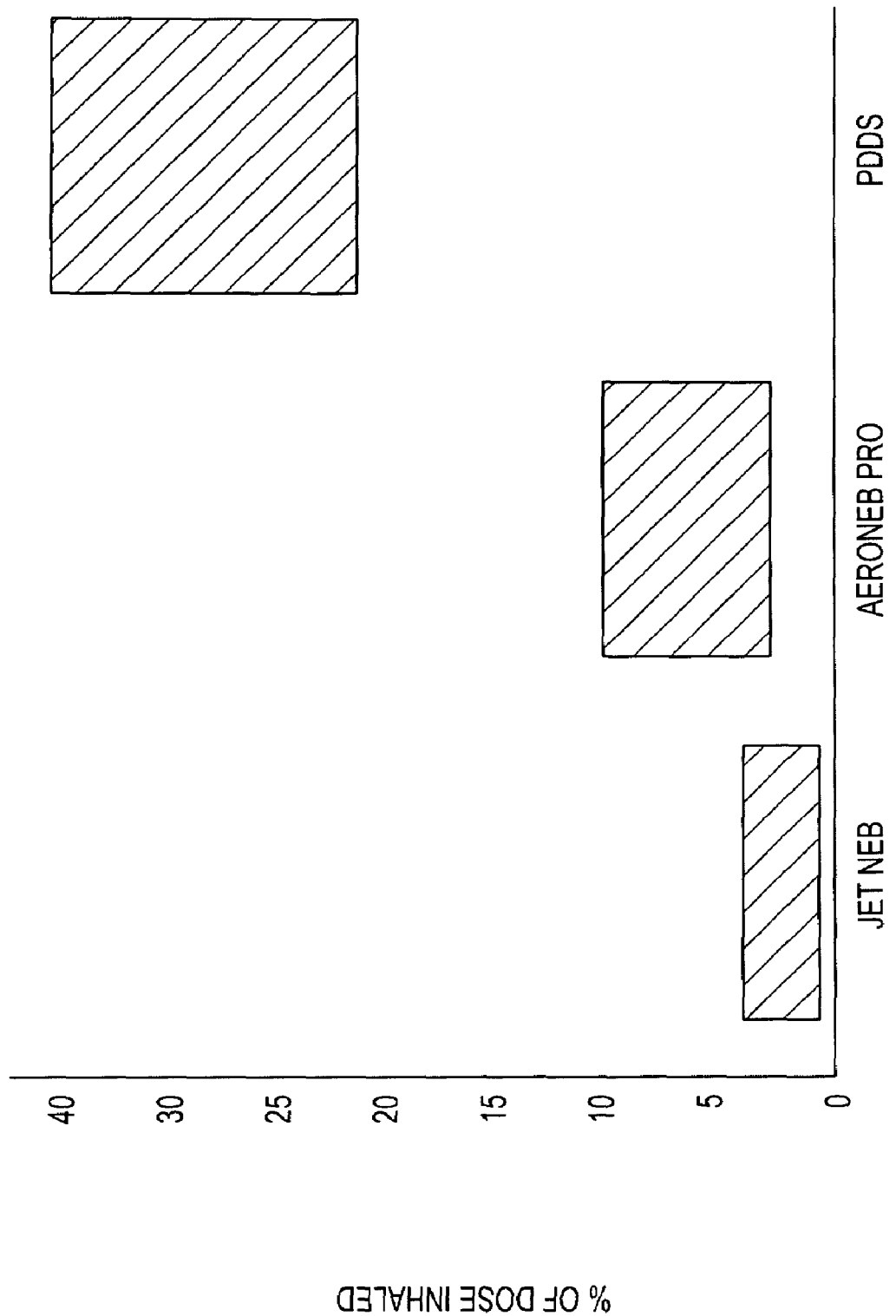
FIG. 8 is a graphic representation showing the range of inhaled mass of three types of nebulizers with nCPAP during simulated infant ventilation using the models of FIGS. 7a and 7b.

As illustrated in FIG. 8, when the Aeroneb® Pro nebulizer incorporating a vibrating aperture-type aerosol generator of the present invention is placed in the pressure-generating circuit of the nCPAP system, it is typically more efficient than a standard jet nebulizer. In addition, when the PDDS nebulizer with a vibrating aperture-type aerosol generator of the present invention is placed between the primary gas flow through the nCPAP system and the simulated patient airway, it typically delivers an order of magnitude more medicament through the nasal prongs to the filter. For example, PDDS nebulizer 206 in the position shown in FIG. 7b typically results in deposition of 26±9% (mean+standard deviation) of the medicament dose placed in the nebulizer with continuous generation of aerosol, and 40+9% of the medicament dose placed in the nebulizer with intermittent generation of aerosol. During continuous generation of aerosol, there is typically a visible amount of aerosol that is driven from the nebulizer into the expiratory limb of the pressure-generating circuit in the nCPAP system. Interrupting aerosol generation during expiration in accordance with one aspect of the present invention eliminates the visual losses and may result in close to a 50% improvement in the percentage of dose inhaled. The relatively low deposition achieved in Example 2, even with a higher efficiency vibrating aperture-type aerosol generator nebulizer, is believed to be due in large part to the dilution of the aerosol output of the nebulizer by the high total flow of gas passing through the nebulizer when the nebulizer is placed in the position shown in FIG. 7a.

As the above examples demonstrate, a nebulizer incorporating a vibrating aperture-type aerosol generator in accordance with the present invention is generally more efficient than a standard jet nebulizer when used to deliver aerosolized surfactant and other medicaments to a patient's airway through a typical CPAP system. In one embodiment of the invention, that efficiency can be even more dramatically improved by placing a particularly preferred small nebulizer including vibrating aperture-type aerosol generator in the lower-flow respiratory circuit of the CPAP system, most preferably in close proximity to the patient's airway. In still another embodiment of the invention, even more efficiency may be achieved by generating the aerosol intermittently, for example, only during inhalation and interrupting generation during exhalation.

It is understood that while the invention has been described above in connection with preferred specific embodiments, the description and drawings are intended to illustrate and not limit the scope of the invention, which is defined by the appended claims and their equivalents.

What is claimed is:

1. In a surfactant replacement therapy wherein a liquid lung surfactant composition is aerosolized and delivered to the lungs of a patient having lung surfactant deficiency or dysfunction, the improvement which comprises:
   aerosolizing the lung surfactant with a vibrating aperture-type aerosol generator; and
   introducing the aerosolized lung surfactant into the gas flow within the respiratory circuit of a CPAP system adapted to be coupled to the patient's respiratory system;
   wherein a higher concentration of aerosolized lung surfactant than generated by the aerosol generator is collected in a plenum chamber located outside the respiratory circuit, and then discharged into the respiratory circuit.

2. A surfactant replacement therapy according to claim 1 wherein the circuit of the pressure-assisted breathing system provides a straight or gently angled path for the flow of aerosol particles from the point at which the aerosol generator introduces the aerosolized lung surfactant into the gas flow to the point at which the aerosolized lung surfactant enters the patient's respiratory system.

3. A surfactant replacement therapy according to claim 1 wherein the plenum chamber has an internal volume of 5–400 ml.

4. A surfactant replacement therapy according to claim 1 wherein the mass of surfactant inhaled by the patient is at least 80% of the surfactant provided to the aerosol generator.

5. A surfactant replacement therapy according to claim 4 wherein the inhaled mass is provided in at least 25% of the time required for a breath actuated nebulizer to provide the same inhaled mass.

6. A surfactant replacement therapy according to claim 1 wherein the CPAP system comprises means for discontinuing the introduction of aerosolized lung surfactant into the gas flow when the patient exhales.

7. A surfactant replacement therapy according to claim 1 wherein the CPAP system has a rebreathed volume, and wherein the rebreathed volume is no more than 5 ml.

8. Apparatus for the delivery of an aerosolized medicament to a patient comprising:
   a pressure-generating circuit having a first gas flow that maintains a positive pressure within the apparatus;
   a patient interface device adapted to be coupled to a patient's respiratory system; a respiratory circuit for providing gas communication between the pressure-generating circuit and the patient's respiratory system, wherein the gas flow in the respiratory circuit is lower volume than the first gas flow;

a plenum chamber located outside of and in gas communication with the respiratory circuit;

a vibrating aperture-type aerosol generator positioned so as to generate aerosolized medicament into the plenum chamber, wherein a concentration of aerosolized medicament is collected in the plenum chamber that is higher than the concentration generated by the aerosol generator;

a conduit from the plenum chamber to a point in the respiratory circuit proximal to the patient's airway; and means for introducing a controlled secondary gas flow into the plenum chamber to drive concentrated aerosolized medicament through the conduit into the gas flow in the respiratory circuit.

9. Apparatus according to claim 8 wherein the plenum chamber has an internal volume of 5–400 ml.

10. Apparatus according to claim 8 wherein the plume of aerosolized medicament generated by the aerosol generator does not impact the bottom or walls of the plenum chamber.

11. Apparatus according to claim 8 wherein the conduit has a one-way valve or conduit that controls the flow of concentrated aerosolized medicament to the respiratory circuit so as to isolate the volume of gas in the plenum chamber from being rebreathed volume.

12. Apparatus according to claim 8 wherein the aerosolized medicament is a lung surfactant.

* * * * *